(12) United States Patent
Grotz et al.

(10) Patent No.: US 8,394,143 B2
(45) Date of Patent: Mar. 12, 2013

(54) SELECTIVELY EXPANDING SPINE CAGE, HYDRAULICALLY CONTROLLABLE IN THREE DIMENSIONS FOR ENHANCED SPINAL FUSION

(75) Inventors: Thomas Grotz, San Francisco, CA (US); Rudy Pretti, Auburn, CA (US)

(73) Assignee: Coalign Innovations, Inc., Brisbane, CA (US)

( * ) Notice: Subject to any disclaimer, the term of this patent is extended or adjusted under 35 U.S.C. 154(b) by 1310 days.

(21) Appl. No.: 11/981,150

(22) Filed: Oct. 31, 2007

(65) Prior Publication Data

US 2008/0147194 A1   Jun. 19, 2008

Related U.S. Application Data

(62) Division of application No. 11/535,432, filed on Sep. 26, 2006.

(60) Provisional application No. 60/720,784, filed on Sep. 26, 2005.

(51) Int. Cl.
*A61F 2/44* (2006.01)
(52) U.S. Cl. .................................. 623/17.11; 623/17.16
(58) Field of Classification Search .......... 606/246–247, 606/90; 623/17.11–17.16
See application file for complete search history.

(56) References Cited

U.S. PATENT DOCUMENTS

| | | | |
|---|---|---|---|
| 3,875,595 A | 4/1975 | Froning | |
| 4,932,975 A | 6/1990 | Main et al. | |
| 4,969,888 A | 11/1990 | Scholten et al. | |
| 5,236,460 A * | 8/1993 | Barber | 623/17.15 |
| 5,653,763 A | 8/1997 | Errico et al. | |
| 5,665,122 A | 9/1997 | Kambin | |
| 5,827,328 A | 10/1998 | Butterman | |
| 5,865,848 A | 2/1999 | Baker | |
| 5,980,522 A | 11/1999 | Koros et al. | |
| 6,039,761 A | 3/2000 | Li et al. | |
| 6,102,950 A | 8/2000 | Vaccaro | |
| 6,127,597 A | 10/2000 | Beyar et al. | |
| 6,176,881 B1 | 1/2001 | Schar et al. | |
| 6,193,756 B1 | 2/2001 | Studer et al. | |
| 6,296,665 B1 | 10/2001 | Strnad et al. | |
| 6,371,989 B1 | 4/2002 | Chauvin et al. | |
| 6,375,682 B1 | 4/2002 | Fleischmann et al. | |
| 6,375,683 B1 | 4/2002 | Crozet et al. | |
| 6,395,032 B1 | 5/2002 | Gauchet | |
| 6,454,806 B1 | 9/2002 | Cohen et al. | |

(Continued)

FOREIGN PATENT DOCUMENTS

| | | |
|---|---|---|
| EP | 1415624 | 5/2004 |
| EP | 1442715 | 8/2004 |

(Continued)

OTHER PUBLICATIONS

Response to Office Action dated Dec. 16, 2010, in related U.S. Appl. No. 11/692,800 entitled "Selectively Expanding Spine Cage, Hydraulically Controllable in Three Dimensions for Vertebral Body Replacement."

(Continued)

*Primary Examiner* — Eduardo C Robert
*Assistant Examiner* — Tara Carter
(74) *Attorney, Agent, or Firm* — Downs Rachlin Martin PLLC

(57) ABSTRACT

A selectively expanding spine cage has a minimized diameter in its unexpanded state that is smaller than the diameter of the neuroforamen through which it passes in the distracted spine. Hydraulic extension of extendable members permit the cage to conformably engage between vertebral bodies to effectively distract the disc space and rigidly fix the spine.

25 Claims, 12 Drawing Sheets

U.S. PATENT DOCUMENTS

| | | | |
|---|---|---|---|
| 6,692,495 B1 * | 2/2004 | Zacouto | 606/247 |
| 6,719,796 B2 | 4/2004 | Cohen et al. | |
| 6,723,126 B1 | 4/2004 | Berry | |
| 6,730,088 B2 | 5/2004 | Yeh | |
| 6,764,491 B2 | 7/2004 | Frey et al. | |
| 6,875,235 B2 * | 4/2005 | Ferree | 623/20.32 |
| 6,981,989 B1 | 1/2006 | Fleischmann et al. | |
| 7,001,431 B2 | 2/2006 | Bao et al. | |
| 7,018,415 B1 | 3/2006 | McKay | |
| 7,018,416 B2 | 3/2006 | Hanson et al. | |
| 7,060,073 B2 | 6/2006 | Frey et al. | |
| 7,094,257 B2 | 8/2006 | Mujwid et al. | |
| 7,166,110 B2 | 1/2007 | Yundt | |
| 7,204,853 B2 | 4/2007 | Gordon et al. | |
| 7,214,243 B2 | 5/2007 | Taylor | |
| 7,217,293 B2 | 5/2007 | Branch, Jr. | |
| 7,282,063 B2 | 10/2007 | Cohen et al. | |
| 7,291,150 B2 | 11/2007 | Graf | |
| 7,291,158 B2 | 11/2007 | Crow et al. | |
| 7,316,686 B2 | 1/2008 | Dorchak et al. | |
| 7,316,714 B2 | 1/2008 | Gordon et al. | |
| 7,351,261 B2 | 4/2008 | Casey | |
| 7,670,359 B2 | 3/2010 | Yundt | |
| 7,722,674 B1 | 5/2010 | Grotz | |
| 7,794,501 B2 | 9/2010 | Edie et al. | |
| 7,819,921 B2 | 10/2010 | Grotz | |
| 7,854,766 B2 | 12/2010 | Moskowitz et al. | |
| 7,985,256 B2 | 7/2011 | Grotz et al. | |
| 2002/0128716 A1 | 9/2002 | Cohen et al. | |
| 2002/0138146 A1 | 9/2002 | Jackson | |
| 2002/0151976 A1 | 10/2002 | Foley et al. | |
| 2003/0114899 A1 | 6/2003 | Woods et al. | |
| 2004/0088054 A1 | 5/2004 | Berry | |
| 2004/0133273 A1 | 7/2004 | Cox | |
| 2005/0043800 A1 | 2/2005 | Paul et al. | |
| 2005/0085910 A1 | 4/2005 | Sweeney | |
| 2005/0113842 A1 | 5/2005 | Bertagnoli et al. | |
| 2005/0197702 A1 | 9/2005 | Coppes et al. | |
| 2005/0216084 A1 | 9/2005 | Fleischmann et al. | |
| 2005/0229433 A1 | 10/2005 | Cachia | |
| 2005/0273169 A1 | 12/2005 | Purcell | |
| 2005/0273170 A1 | 12/2005 | Navarro et al. | |
| 2005/0273171 A1 | 12/2005 | Gordon et al. | |
| 2006/0036259 A1 | 2/2006 | Carl et al. | |
| 2006/0085073 A1 | 4/2006 | Raiszadeh | |
| 2006/0106416 A1 | 5/2006 | Raymond et al. | |
| 2006/0116767 A1 | 6/2006 | Magerl et al. | |
| 2006/0149377 A1 | 7/2006 | Navarro et al. | |
| 2006/0167547 A1 | 7/2006 | Suddaby | |
| 2006/0200244 A1 | 9/2006 | Assaker | |
| 2006/0235426 A1 | 10/2006 | Lim et al. | |
| 2006/0235535 A1 | 10/2006 | Ferree et al. | |
| 2006/0264968 A1 | 11/2006 | Frey et al. | |
| 2007/0050030 A1 | 3/2007 | Kim | |
| 2007/0050033 A1 | 3/2007 | Reo et al. | |
| 2007/0073395 A1 | 3/2007 | Baumgartner et al. | |
| 2007/0093901 A1 | 4/2007 | Grotz et al. | |
| 2007/0093903 A1 | 4/2007 | Cheng | |
| 2007/0123987 A1 | 5/2007 | Bernstein | |
| 2007/0179611 A1 | 8/2007 | DiPoto et al. | |
| 2007/0233254 A1 | 10/2007 | Grotz | |
| 2007/0255409 A1 | 11/2007 | Dickson et al. | |
| 2007/0255413 A1 | 11/2007 | Edie et al. | |
| 2007/0255415 A1 | 11/2007 | Edie et al. | |
| 2007/0288092 A1 | 12/2007 | Bambakidis | |
| 2008/0058930 A1 | 3/2008 | Edie et al. | |
| 2008/0065082 A1 | 3/2008 | Chang et al. | |
| 2008/0077150 A1 | 3/2008 | Nguyen | |
| 2008/0103601 A1 | 5/2008 | Biro et al. | |
| 2008/0114467 A1 | 5/2008 | Capote et al. | |
| 2008/0147194 A1 | 6/2008 | Grotz et al. | |
| 2008/0161933 A1 | 7/2008 | Grotz et al. | |
| 2008/0177387 A1 | 7/2008 | Parimore et al. | |
| 2008/0281424 A1 | 11/2008 | Parry et al. | |
| 2008/0300598 A1 | 12/2008 | Barreiro et al. | |
| 2009/0043312 A1 | 2/2009 | Koulisis et al. | |
| 2009/0204215 A1 | 8/2009 | McClintock et al. | |
| 2009/0216331 A1 | 8/2009 | Grotz et al. | |
| 2009/0222100 A1 | 9/2009 | Cipoletti et al. | |
| 2009/0270987 A1 | 10/2009 | Heinz et al. | |
| 2010/0057204 A1 | 3/2010 | Kadaba | |
| 2010/0145455 A1 | 6/2010 | Simpson et al. | |
| 2011/0130835 A1 | 6/2011 | Ashley et al. | |
| 2011/0270398 A1 | 11/2011 | Grotz et al. | |
| 2011/0288646 A1 | 11/2011 | Moskowitz et al. | |
| 2012/0245695 A1 | 9/2012 | Simpson et al. | |

FOREIGN PATENT DOCUMENTS

| | | |
|---|---|---|
| WO | 2004016250 | 2/2004 |
| WO | WO 2004/016250 | 2/2004 |
| WO | WO 2008/011371 | 1/2008 |
| WO | 2008039811 | 4/2008 |
| WO | 2008121251 | 10/2008 |
| WO | 2009105182 | 8/2009 |
| WO | 2010068725 | 6/2010 |
| WO | 2011150077 | 12/2011 |

OTHER PUBLICATIONS

Terminal Disclaimer dated Dec. 16, 2010, in related U.S. Appl. No. 11/692,800 entitled "Selectively Expanding Spine Cage, Hydraulically Controllable in Three Dimensions for Vertebral Body Replacement."

Restriction Requirement dated Dec. 27, 2010, in related U.S. Appl. No. 12/072,044 entitled "Spinal Implant With Expandable Fixation."

Amendment and Response to Restriction Requirement dated Jan. 27, 2011, in related U.S. Appl. No. 12/072,044 entitled "Spinal Implant With Expandable Fixation."

International Search Report and Written Opinion dated Nov. 11, 2010, in International Application No. PCT/US2010/031247 entitled "Insertion Handle for Implant."

Final Office Action dated Feb. 1, 2011, in related U.S. Appl. No. 11/535,432 entitled "Selectively Expanding Spine Cage, Hydraulically Controllable in Three Dimensions for Enhanced Spinal Fusion."

Final Office Action dated Mar. 2, 2011, in related U.S. Appl. No. 11/692,800 entitled "Selectively Expanding Spine Cage, Hydraulically Controllable in Three Dimensions for Vertebral Body Replacement."

Response to Final Office Action dated Mar. 23, 2011, in related U.S. Appl. No. 11/535,432 entitled "Selectively Expanding Spine Cage, Hydraulically Controllable in Three Dimensions for Enhanced Spinal Fusion."

International Search Report for PCT/US2007/079474 mailed Apr. 10, 2008.

Written Opinion of the International Searching Authority for PCT/US2007/079474 mailed Apr. 10, 2008.

Related U.S. Appl. No. 11/535,432, filed Sep. 26, 2006, in the name of Thomas Grotz et al., titled "Selectively Expanding Spine Cage, Hydraulically Controllable in Three Dimensions for Enhanced Spinal Fusion."

Related U.S. Appl. No. 12/787,281, filed May 25, 2010, in the name of John E. Ashley et al., titled "Adjustable Distraction Cage with Linked Locking Mechanism."

Related U.S. Appl. No. 12/380,840, filed Mar. 4, 2009, in the name of Philip J. Simpson et al., titled "Lockable Spinal Implant."

Related International Application No. PCT/US2009/067446 filed Dec. 10, 2009, in the name of Innvotec Surgical, Inc., titled "Lockable Expanding Spine Cage."

International Search Report and Written Opinion dated Aug. 13, 2010, in related International Application No. PCT/US2009/067446 filed Dec. 10, 2009.

Related International Application No. PCT/US2009/00974 filed Feb. 17, 2009, in the name of Innvotec Surgical, Inc., titled "Spinal Implant with Expandable Fixation."

International Search Report and Written Opinion dated May 6, 2009, in related International Application No. PCT/US2009/000974 filed Feb. 17, 2009.

Related International Application No. PCT/US2008/003776 filed Mar. 21, 2008, in the name of Innvotec Surgical, Inc., titled "Selectively Expanding Spine Cage, Hydraulically Controllable in Three Dimensions for Vertebral Body Replacement."

International Search Report and Written Opinion dated Jun. 30, 2009, in related International Application No. PCT/US2008/003776 filed Mar. 21, 2008.
Related U.S. Appl. No. 11/692,800, filed Mar. 28, 2007, in the name of R. Thomas Grotz et al., titled "Selectively Expanding Spine Cage, Hydraulically Controllable in Three Dimensions for Vertebral Body Replacement."
Office Action dated Sep. 16, 2010 in related U.S. Appl. No. 11/692,800, filed Mar. 28, 2007, in the name of R. Thomas Grotz et al., titled "Selectively Expanding Spine Cage, Hydraulically Controllable in Three Dimensions for Vertebral Body Replacement."
Related U.S. Appl. No. 12/072,044, filed Feb. 22, 2008, in the name of R. Thomas Grotz et al., titled "Spinal Implant with Expandable Fixation."
Related U.S. Appl. No. 12/548,260, filed Aug. 26, 2009, in the name of Murali Kadaba et al., titled "Hydraulically Actuated Expanding Spine Cage with Extendable Locking Anchor."
Related U.S. Appl. No. 11/981,452, filed Oct. 31, 2007, in the name of R. Thomas Grotz et al., titled "Selectively Expanding Spine Cage, Hydraulically Controllable in Three Dimensions for Vertebral Body Replacement."
Related U.S. Appl. No. 12/384,622, filed Apr. 7, 2009, in the name of Philip J. Simpson et al., titled "Lockable Spinal Implant."
Preliminary Amendment dated Dec. 4, 2007 in related U.S. Appl. No. 11/535,432, titled "Selectively Expanding Spine Cage, Hydraulically Controllable in Three Dimensions for Enhanced Spinal Fusion."
Second Preliminary Amendment dated Mar. 18, 2008 in related U.S. Appl. No. 11/535,432, titled "Selectively Expanding Spine Cage, Hydraulically Controllable in Three Dimensions for Enhanced Spinal Fusion."
Third Preliminary Amendment dated Aug. 7, 2008 in related U.S. Appl. No. 11/535,432, titled "Selectively Expanding Spine Cage, Hydraulically Controllable in Three Dimensions for Enhanced Spinal Fusion."
Restriction Requirement dated Mar. 17, 2010 in related U.S. Appl. No. 11/535,432, titled "Selectively Expanding Spine Cage, Hydraulically Controllable in Three Dimensions for Enhanced Spinal Fusion."
Response to Restriction Requirement dated Mar. 31, 2010 in related U.S. Appl. No. 11/535,432, titled "Selectively Expanding Spine Cage, Hydraulically Controllable in Three Dimensions for Enhanced Spinal Fusion."
Office Action dated Jul. 9, 2010 in related U.S. Appl. No. 11/535,432, titled "Selectively Expanding Spine Cage, Hydraulically Controllable in Three Dimensions for Enhanced Spinal Fusion."
Response to Office Action dated Oct. 4, 2010 in related U.S. Appl. No. 11/535,432, titled "Selectively Expanding Spine Cage, Hydraulically Controllable in Three Dimensions for Enhanced Spinal Fusion."
Preliminary Amendment dated Dec. 11, 2009 in related U.S. Appl. No. 12/548,260, titled "Hydraulically Actuated Expanding Spine Cage with Extendable Locking Anchor."
Preliminary Amendment dated Oct. 31, 2007 in related U.S. Appl. No. 11/981,452, filed Oct. 31, 2007, titled "Selectively Expanding Spine Cage, Hydraulically Controllable in Three Dimensions for Vertebral Body Replacement."
International Search Report and Written Opinion dated Apr. 10, 2008, in related International Application No. PCT/US2007/079474.
Office Action dated Mar. 31, 2011, in related U.S. Appl. No. 11/981,452 entitled "Selectively Expanding Spine Cage, Hydraulically Controllable in Three Dimensions for Vertebral Body Replacement."
Restriction Requirement dated Apr. 4, 2011, in related U.S. Appl. No. 12/384,622 entitled "Lockable Spinal Implant."
Notice of Allowance dated Apr. 13, 2011, in related U.S. Appl. No. 11/535,432, entitled "Selectively Expanding Spine Cage, Hydraulically Controllable in Three Dimensions for Enhanced Spinal Fusion."
Restriction Requirement dated May 2, 2011, in related U.S. Appl. No. 12/380,840 entitled "Lockable Spinal Implant."
Response to Final Office Action dated May 2, 2011, in related U.S. Appl. No. 11/692,800 entitled "Selectively Expanding Spine Cage, Hydraulically Controllable in Three Dimensions for Vertebral Body Replacement."
Related U.S. Appl. No. 13/183,080, filed Jul. 14, 2011, in the name of Thomas Grotz et al., entitled "Selectively Expanding Spine Cage, Hydraulically Controllable in Three Dimensions for Enhanced Spinal Fusion."
Notice of Allowance dated Aug. 3, 2011, in related U.S. Appl. No. 11/692,800, entitled "Selectively Expanding Spine Cage, Hydraulically Controllable in Three Dimensions for Vertebral Body Replacement."
Response to Office Action dated Aug. 9, 2011, in related U.S. Appl. No. 12/072,044, entitled "Spinal Implant With Expandable Fixation."
Office Action dated Aug. 31, 2011, in related U.S. Appl. No. 12/384,622, entitled "Lockable Spinal Implant."
Office Action dated May 9, 2011, in related U.S. Appl. No. 12/072,044 entitled "Spinal Implant With Expandable Fixation."
Response to Restriction Requirement dated Jun. 6, 2011, in related U.S. Appl. No. 12/384,622 entitled "Lockable Spinal Implant."
Related International Application No. PCT/US2011/037929 filed May 25, 2011, entitled "Adjustable Distraction Cage With Linked Locking Mechanisms."
Office Action dated Apr. 26, 2011, in related CN Application No. 200880016846.7, entitled "Selectively Expanding Spine Cage, Hydraulically Controllable in Three Dimensions for Vertebral Body Replacement."
Advisory Action dated May 19, 2011, in related U.S. Appl. No. 11/692,800, entitled "Selectively Expanding Spine Cage, Hydraulically Controllable in Three Dimensions for Vertebral Body Replacement."
Amendment After Final Office Action dated Jul. 5, 2011, in related U.S. Appl. No. 11/692,800, entitled "Selectively Expanding Spine Cage, Hydraulically Controllable in Three Dimensions for Vertebral Body Replacement."
Office Action dated Apr. 9, 2012, in related U.S. Appl. No. 12/787,281, filed May 25, 2010.
Notice of Allowance dated Feb. 23, 2012, in related U.S. Appl. No. 12/384,622, filed Apr. 7, 2009.
Restriction Requirement dated Feb. 27, 2012, in related U.S. Appl. No. 12/787,281, filed May 25, 2010.
Response to Restriction Requirement dated Mar. 27, 2012, in related U.S. Appl. No. 12/787,281, filed May 25, 2010.
Response to Restriction Requirement dated Mar. 12, 2012, in related U.S. Appl. No. 12/548,260, filed Aug. 26, 2009.
Response to Office Action dated Feb. 17, 2012, in related U.S. Appl. No. 12/072,044, filed Feb. 22, 2008.
Advisory Action dated Mar. 12, 2012, in related U.S. Appl. No. 12/072,044, filed Feb. 22, 2008.
Response to Final Office Action dated Mar. 19, 2012, in related U.S. Appl. No. 12/072,044, filed Feb. 22, 2008.
Office Action dated Mar. 29, 2012, in related U.S. Appl. No. 12/072,044, filed Feb. 22, 2008.
Restriction Requirement dated Jan. 10, 2012, in related U.S. Appl. No. 12/548,260 entitled "Hydraulically Actuated Expanding Spine Cage with Extendable Locking Anchor."
Examination Report dated Oct. 18, 2011 in related EU Application No. 08727082.3 in the name of CoAlign Innovations, Inc.
International Search Report and Written Opinion dated Sep. 22, 2011 in related International Application No. PCT/US2011/037929.
Final Office Action dated Nov. 18, 2011 in related U.S. Appl. No. 12/072,044, filed Feb. 22, 2008.
Response to Office Action filed Nov. 18, 2011 in related U.S. Appl. No. 12/384,622, filed Apr. 7, 2009.
Translated Second Office Action dated Apr. 26, 2012 in related China Application No. 200880016846.7.
Office Action dated Jun. 20, 2012, in related U.S. Appl. No. 13/183,080, filed Jul. 14, 2011.
Office Action dated Jun. 20, 2012, in related U.S. Appl. No. 13/311,487, filed Dec. 5, 2011.
Office Action dated Jun. 1, 2012, in related U.S. Appl. No. 12/548,260, filed Aug. 26, 2009.

Response to Office Action dated Jul. 30, 2012, in related U.S. Appl. No. 12/072,044, filed Feb. 22, 2008.
Examination Report dated Jul. 17, 2012, in European Patent Application No. 09712948.0.
Response to Office Action dated Oct. 9, 2012, in related U.S. Appl. No. 12/787,281, filed May 25, 2010.
Response to Office Action dated Oct. 15, 2012, in related U.S. Appl. No. 12/548,260, filed Aug. 26, 2009.
Response to Office Action dated Oct. 22, 2012, in connection with related U.S. Appl. No. 13/183,080, filed Jul. 14, 2011.
Supplemental Response to Final Office Action dated Jan. 4, 2013, in connection with related U.S. Appl. No. 12/548,260, filed Aug. 26, 2009.
Response to Office Action dated Oct. 22, 2012, in connection with related U.S. Appl. No. 13/311,487, filed Dec. 5, 2011.
Response to Office Action dated Oct. 9, 2012, in connection with related U.S. Appl. No. 12/787,281, filed May 25, 2010.
Final Office Action dated Jan. 2, 2013, in connection with related U.S. Appl. No. 12/787,281, filed May 25, 2010.
Final Office Action dated Nov. 19, 2012, in connection with related U.S. Appl. No. 12/072,044, filed Feb. 22, 2008.
Response to Office Action dated Oct. 15, 2012, in connection with related U.S. Appl. No. 12/548,260, filed Aug. 26, 2009.
Final Office Action dated Oct. 30, 2012, in connection with related U.S. Appl. No. 12/548,260, filed Aug. 26, 2009.
Response to Final Office Action dated Dec. 31, 2012, in connection with related U.S. Appl. No. 12/548,260, filed Aug. 26, 2009.

* cited by examiner

SELECTIVELY EXPANDING SPINE CAGE, HYDRAULICALLY CONTROLLABLE IN THREE DIMENSIONS FOR ENHANCED SPINAL FUSION

RELATED APPLICATIONS

This application is a divisional of application Ser. No. 11/535,432, filed Sep. 26, 2006, which is incorporated herein its entirety by reference and from which priority is claimed. Application Ser. No. 11/535,432 also claims priority benefit to provisional application Ser. No. 60/720,784, filed Sep. 26, 2005.

BACKGROUND

Field of the Invention

The field of the invention relates to medical devices for stabilizing the vertebral motion segment. More particularly, the field of the invention relates to a remotely activated, hydraulically controllable, selectively expanding cage (SEC) and method of insertion for providing controlled spinal correction in three dimensions for improved spinal intervertebral body distraction and fusion.

Current Inability to Expand and Distract Endplates

A conventional spine cage or implant is characterized by a kidney bean shaped body comprising a hydroxyapetite coated surface provided on the exterior surface for contact with adjacent vertebral segments or endplates which are shown in FIG. 1. A conventional spine cage is typically inserted in tandem posteriorly through the neuroforamen of the distracted spine after a trial implant creates a pathway.

Such existing devices for interbody stabilization have important and significant limitations. These limitations include an inability to expand and distract the endplates. Current devices for interbody stabilization include static spacers composed of titanium, PEEK, and high performance thermoplastic polymer produced by VICTREX, (Victrex USA Inc, 3A Caledon Court; Greenville, S.C. 29615), carbon fiber, or resorbable polymers. Current interbody spacers do not maintain interbody lordosis and can contribute to the formation of a straight or even kyphotic segment and the clinical problem of "flatback syndrome." Separation of the endplates increases space available for the neural elements, specifically the neural foramen. Existing static cages do not reliably improve space for the neural elements. Therefore, what is needed is an expanding cage that will increase space for the neural elements posteriorly between the vertebral bodies, or at least maintain the natural bone contours to avoid neuropraxia (nerve stretch) or encroachment.

Poor Interface between Bone and Biomaterial

Another problem with conventional devices of interbody stabilization includes poor interface between bone and biomaterial. Conventional static interbody spacers form a weak interface between bone and biomaterial. Although the surface of such implants is typically provided with a series of ridges or coated with hydroxyapetite, the ridges may be in parallel with applied horizontal vectors or side-to-side motion. That is, the ridges or coatings offer little resistance to movement applied to either side 104 of the endplates. Thus, nonunion is common in allograft, titanium and polymer spacers, due to motion between the implant and host bone. Conventional devices typically do not expand between adjacent vertebrae.

Therefore, what is needed is a way to expand an implant to develop immediate fixation forces that can exceed the ultimate strength at healing. Such an expandable implant ideally will maximize stability of the interface and enhance stable fixation. The immediate fixation of such an expandable interbody implant advantageously will provide stability that is similar to that achieved at the time of healing. Such an implant would have valuable implications in enhancing early postoperative rehabilitation for the patient.

Conventional Large Size Static Devices Require Wide Exposure of Neural Structures Another problem of conventional interbody spacers is their large diameter requiring wide exposure. Existing devices used for interbody spacers include structural allograft, threaded cages, cylindrical cages, and boomerang-shaped cages. Conventional devices have significant limitation with regard to safety and efficacy. Regarding safety of the interbody spacers, injury to neural elements may occur with placement from an anterior or posterior approach. A conventional spine cage lacks the ability to expand, diminishing its fixation capabilities.

The risks to neural elements are primarily due to the disparity between the large size of the cage required to adequately support the interbody space, and the small space available for insertion of the device, especially when placed from a posterior or transforaminal approach. Existing boomerang cages are shaped like a partially flattened kidney bean. Their implantation requires a wide exposure and potential compromise of vascular and neural structures, both because of their inability to enter small and become larger, and due to the fact that their insertion requires mechanical manipulation during insertion and expanding of the implant. Once current boomerang implants are prepared for insertion via a trial spacer to make a pathway toward the anterior spinal column, the existing static cage is shoved toward the end point with the hope that it will reach a desired anatomic destination. Given the proximity of nerve roots and vascular structures to the insertion site, and the solid, relatively large size of conventional devices, such constraints predispose a patient to foraminal (nerve passage site) encroachment, and possible neural and vascular injury.

Therefore, what is needed is a minimally invasive expanding spine cage that is capable of insertion with minimal invasion into a smaller aperture. Such a minimally invasive spine cage advantageously could be expanded with completely positional control or adjustment in three dimensions by hydraulic force application through a connected thin, pliable hydraulic line. The thin hydraulic line would take the place of rigid insertional tools, thereby completely preventing trauma to delicate nerve endings and nerve roots about the spinal column. Due to the significant mechanical leverage developed by a hydraulic control system, the same expanding cage could advantageously be inserted by a minimally sized insertion guiding rod tool capable of directing the cage through the transforaminal approach to a predetermined destination, also with reduced risk of trauma to nerve roots. That is, the mechanical advantage is provided by a hydraulic control system controlled by the physician external to the patient.

The minimally sized insertion tool could house multiple hydraulic lines for precise insertion and expansion of the cage, and simply detached from the expanded cage after insertion. It is noted that in such a hydraulic system, a smaller, thinner line advantageously also increases the pounds per inch of adjusting force necessary to achieve proper expansion of the implant (as opposed to a manually powered or manipulated surgical tool) that must apply force directly at the intervention site. That is, for a true minimally invasive approach to spinal implant surgery what is needed is an apparatus and method for providing the significant amount of force necessary to properly expand and adjust the cage against the vertebral endplates, safely away from the intervention site.

What is also needed is a smaller expanding spine cage that is easier to operatively insert into a patient with minimal surgical trauma in contrast to conventional, relatively large devices that create the needless trauma to nerve roots in the confined space of the vertebral region.

Limited Capacity for Interbody Bone Formation

Existing interbody implants have limited space available for bone graft. Adequate bone graft or bone graft substitute is critical for a solid interbody arthrodesis. It would be desirable to provide an expandable interbody cage that will permit a large volume of bone graft material to be placed within the cage and around it, to fill the intervertebral space. Additionally, conventional interbody implants lack the ability to stabilize endplates completely and prevent them from moving. Therefore, what is also needed is an expanding spine cage wherein the vertebral endplates are subject to forces that both distract them apart, and hold them from moving. Such an interbody cage would be capable of stabilization of the motion segment, thereby reducing micro-motion, and discouraging the pseudoarthrosis (incomplete fusion) and pain.

Ideally, what is needed is a spine cage or implant that is capable of increasing its expansion in width anteriorly to open like a clam, spreading to a calculated degree. Furthermore, what is needed is a spine cage that can adjust the amount of not only overall anterior expansion, but also medial and lateral variable expansion so that both the normal lordotic curve is maintained, and adjustments can be made for scoliosis or bone defects. Such a spine cage or implant would permit restoration of normal spinal alignment after surgery and hold the spine segments together rigidly, mechanically, until healing occurs.

What is also needed is an expanding cage or implant that is capable of holding the vertebral or joint sections with increased pullout strength to minimize the chance of implant fixation loss during the period when the implant is becoming incorporated into the arthrodesis bone block.

It would also be desirable if such a cage could expand anteriorly away from the neural structures and along the axis of the anterior spinal column, rather than uniformly which would take up more space inside the vertebral body surfaces.

SUMMARY

In order to overcome the foregoing disadvantages of conventional spinal implants, an aspect of the invention provides a minimally invasive expanding spinal implant also referred to herein as a selectively expanding spine cage (SEC) for posterior insertion between superior and inferior vertebral end plates. The SEC implant defines an interior cavity for receiving osteoconductive material to promote the formation of new bone in the intervertebral space. The implant is also selectively expandable to restore disc height between adjacent vertebrae and to provide corrective spinal alignment in three dimensions.

The SEC in its first or unexpanded state is approximately 0.8-1 cm in diameter so as to enable minimally invasive insertion posteriorly between vertebral pedicles in a working space approximately 1 cm in diameter. The implant is activated hydraulically, at a master cylinder or with a syringe located remotely form the patient to enable controlled spinal correction in three dimensions.

The SEC implant comprises a 6-4 titanium alloy cylinder block defining two or more cylinders and a central cavity for infusion of bone graft material from a remote source. Titanium pistons are provided in the cylinders and are activated independently and hydraulically from the remotely located master cylinder or syringe.

Once inserted between the endplates, the implant advantageously can be expanded with a minimum of force exerted remotely through the hydraulic control lines. The expansion advantageously is 60% greater than the unexpanded height, or to 13 mm in the case of a 8 mm implant or 16 mm in the case of a 10 mm implant.

A bone engaging plate or optional wedge plate is held in free floating captured engagement on the top of the pistons for imparting a desired anterior/posterior correction angle through vertical expansion of the pistons. Since the vertebral end plates are held together at one end by a ligament much like a clamshell, as the pistons expand vertically against the end plates the amount of vertical expansion of the pistons can be adjusted to create the desired anterior/posterior correction angle.

An optional lordosis or base plate may be provided as a base for the slave cylinder block, resting on the second vertebral end plate. The optional lordosis plate is angled like a wedge to provide a lordosis correction angle in a range of from 0-5 degrees or more. When an extreme anterior/posterior correction angle is desired, the top plate and/or optional base plate may be configured as a wedge to impart an additional anterior/posterior angle of up to 20 degrees.

Left and right lateral correction of the spine is achieved by differential vertical expansion of the two or more cylinders. Each piston is independently controlled by a master cylinder or syringe located ex vivo (away from the patient) and communicating hydraulically with the slave cylinders for moving the pistons and top plate vertically and laterally for correcting spinal deformities anteriorly or posteriorly, medial or lateral, thus providing spinal correction in three dimensions.

The cylinder block and corresponding pistons comprise preferably type 6-4 titanium alloy for extreme strength and compatibility with bone. The cylinder block also defines a central cavity having an inlet for receiving a quantity of bone graft material from a supply line having a connection to a remote source for supplying the bone graft material under pressure to the cavity. The central cavity extends through the cylinder block adjacent both end plates such that as the pistons expand, bone graft material is transfused under appropriate pressure through the cavity to fill a desired space between the end plates.

In accordance with another aspect of the invention, the hydraulic fluid communicating the mechanical leverage from the master cylinder to the slave cylinder advantageously is a time-controlled curable polymer such as methylmethacrylate. The viscosity and curing time can be adjusted by the formulation of an appropriate added catalyst as is well known. When the polymer cures, it hardens and locks the pistons and thus the desired amount of anterior/posterior, medial/lateral, superior/inferior spinal correction immovably in place.

Thus, a key feature of the invention is that an essentially incompressible titanium implant can be inserted posteriorly between vertebral pedicles in only a 1 cm working space. The implant then can be expanded to 160% of its original insertion size to provide a closely controlled full range of spinal correction in three dimensions. Confinement of the hydraulic medium by the rigid titanium alloy cylinder block makes the cured polymer substantially impervious to compressive forces, resulting in a much stronger implant than is conventionally possible. Advantageously, the use of the present 6-4 titanium cylinder block configuration is able to withstand compressive forces in excess of 12,000 Newtons or approximately 3000 pounds of compressive force on the vertebrae. This is not possible in a conventional expanding implant wherein an expanding polymer is not confined by an essentially incompressible titanium body. Further, there is no deterioration of the curable polymer over time in term of its structural integrity because it is confined in the titanium alloy body or cylinder block of the implant. Also, given the adjustable nature of the implant against bone modulated by "the surgeon's touch or sense of pressure applied" throughout the trial and later actual piston expansion process, tendency toward bone endplate injury and ultimate subsidence is reduced. The tactile advantage is thus realized as a fluid such as saline from a syringe to the pistons during trial expansion is used. Thereafter, the liquid (methylmethacrylate polymer) for final expansion is used for final precalculated expansion via new syringes using gauges, roentgenograms, clinical appearance and the sense of pressure against the vertebral bodies to create the desired safe and corrective SEC widening effects. In a conventional implant system, no such pressurized adjustments are available.

In another aspect of the invention, multiple slave cylinders and pistons are provided (with or without a top plate) in the SEC implant. The multiple slave pistons provide a three-dimensional corrective surface. Each slave piston in the SEC communicates hydraulically with a corresponding one of a plurality of cylinders in the remotely located master cylinder for independently controlled expansion of the slave cylinders at multiple elevations in three dimensions (X, Y and Z axes).

The surgeon adjusts the master cylinder or syringe to provide a controlled angle to the medial/lateral (X axis) anterior, anterior/posterior (Z axis) and can adjust the SEC superiorly/inferiorly for vertical adjustment (Y axis). Thus, three-dimensional control is achieved remotely through hydraulic lines with minimal trauma to a patient.

The master cylinder or separate source also advantageously provides injectable bone graft material over a line to an input port in the SEC and thence to a cavity provided in the slave cylinder block for filling of the SEC and post-expansion space between adjacent vertebral bodies. This achieves substantially complete perfusion of osteo-inductive and osteo-conductive bone graft material in the post expansion space between the vertebral bodies resulting in enhanced fusion.

A minimally invasive downsized insertion tool both inserts the unexpanded SEC posteriorly and houses the hydraulic lines communicating between the master cylinder and the slave cylinder. The insertion tool also houses a line for communicating the liquid or slurry bone graft material to the slave cylinder and into the intervertebral space. Advantageously, thin hydraulic lines are utilized. Small size tubing for the hydraulic lines advantageously allows high hydraulic pressure without danger of the lines bursting. The sizes of the slave cylinders and pistons can be varied to increase the mechanical advantage.

In accordance with an aspect of the invention, the master cylinder comprises one or more threaded pistons which are screwed down into corresponding cylinders in order to provide the mechanical advantage. In this case, the pitch of the thread controls the rotation pressure and thus mechanical advantage. For example, with ten threads per inch, ten turns of a knob or piston are necessary to move one inch. Twenty threads would require twenty turns per inch, but the rotation force would be 50% less. A finer pitch thread provides 50 percent more upward force to the slave cylinder with the same rotational torque at the master cylinder. Typically, the master cylinder achieves from 200-500 psi. As is well known the slave cylinders can be larger than the master cylinder to increase the pressure (psi) and thus the expansion force in the slave cylinder. Other advantages of the system include the following:

The master cylinder is a disposable item made of clear acrylic material.

The handle of the insertion tool is disposable and easily can be disassembled when polymer is hardened.

The master cylinder mechanism is either a lever or a threaded screw device or syringe. Such threaded master cylinder pistons or their equivalent are rotated to raise the slave pistons with a mechanical advantage provided by the screw pitch of the threads as explained above.

Hydraulic lines access slave pistons through an insertion tool with direct connection between a master and slave cylinder without check valves.

The hydraulic control system provides a minimally invasive procedure by enabling the surgeon to apply a controlling force away from the patient's body to expand and adjust the spinal implant in three dimensions. (Infinitely adjustable height and lateral angles, not limited to incremental positions)

The wedge plate provides anterior/posterior spinal correction from 0-20 degrees right or left. The optional base or lordosis plate is also angled approximately 0-20 degrees (anterior/posterior) to correct lordosis angle anterior to posterior.

The slave cylinder has an air bleed valve that serves to allow filling of cylinder ex vivo (outside the body).

Due to the mechanical advantage provided by the hydraulic system, the SEC has minimized size and diameter in its unexpanded state that is smaller than the diameter of a prepared neuroforamen. The SEC thus can be inserted posteriorly and is engaged between the endplates of the adjacent vertebra to effectively distract the intervertebral area, restore space for neural elements, stabilize the motion segment and eliminate pathologic segmental motion. The SEC enhances spine arthrodesis by creating a rigid spine segment.

The SEC provides a significant advantage by enabling a comparatively large quantity of bone growth conductive or inductive agents to be contained within its interior and communicating directly to adjacent bone. Importantly, this results in fixation forces greater than adjacent bone and soft tissue failure forces.

It will be appreciated that the corrective surface formed by the wedge plate maintains a constant angle as it expands. Generally, one SEC is used for fusion through the posterior approach—though the surgeon can choose any insertional vector. The cage can be used as a cage or spacer, to promote fusion, and/or to correct deformities such as scoliosis, kyphosis, and spondylolisthesis.

The clinical goals of the SEC and the method for its insertion provide a minimally invasive risk of trauma to nerve roots, reduce pain, improve function, and permit early mobilization of the patient after fusion surgery. Once healing (fusion or arthrodesis) does occur, the implants become incorporated inside bone and their role becomes quiescent.

The present SEC provides more internal and external graft bone space exposure, easier and safer directed insertion, less risk of insertional damage to nerve roots and other tissue, and thus a substantially improved immediate and long term result.

BRIEF DESCRIPTION OF THE DRAWINGS

The drawings are heuristic for clarity. The foregoing and other features, aspects and advantages of the invention will become better understood with reference to the following descriptions, appended claims and accompanying drawings in which:

DETAILED DESCRIPTION

Figure 1:
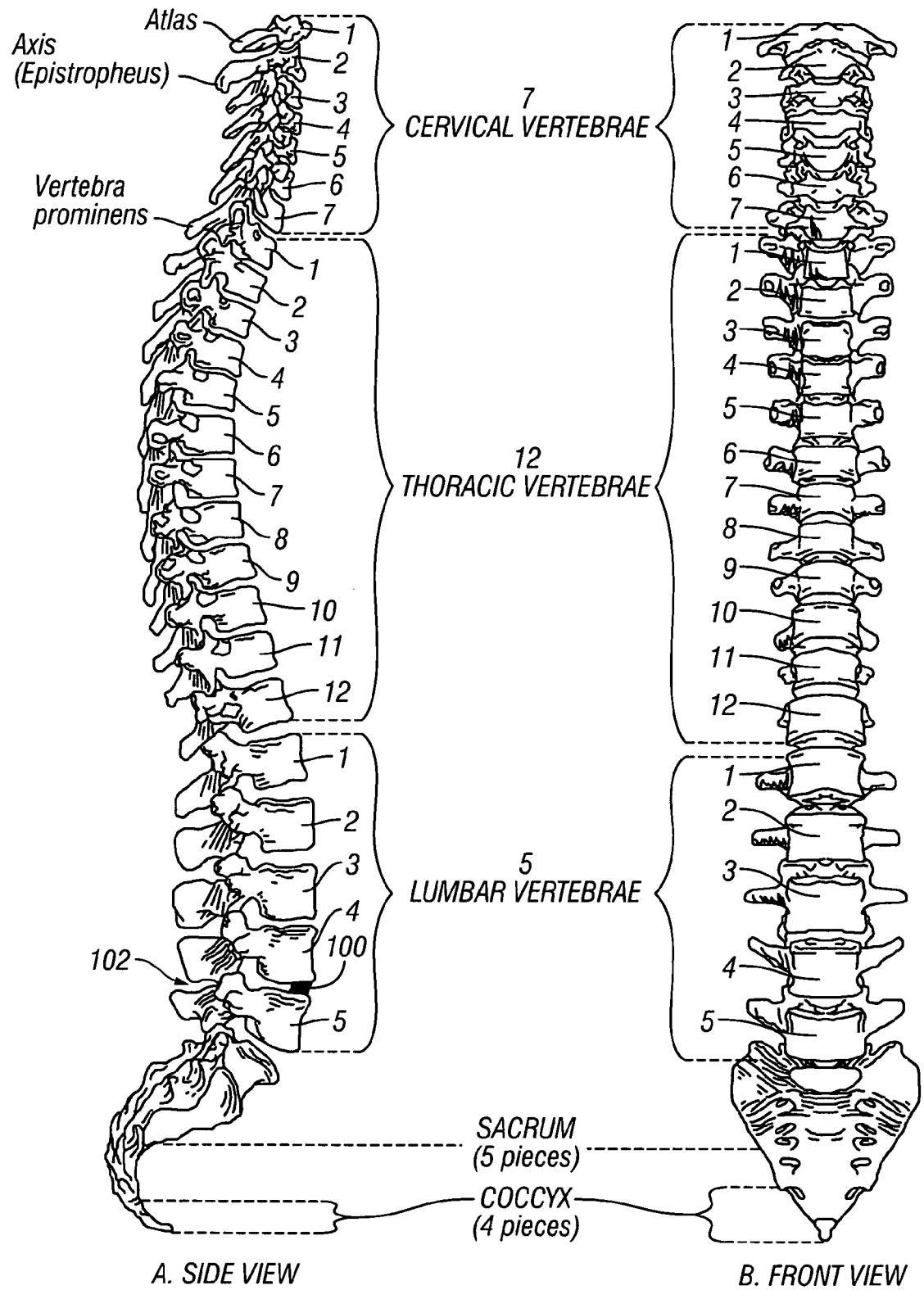
FIG. 1 is a representation of the vertebral column showing posterior insertion and placement of the SEC between the number 4 and 5 lumbar vertebrae according to an aspect of the invention. Whereas this diagram shows the implant anteriorly in the vertebral interspace between lumbar bones 4 and 5, the majority of lumbar fusions are performed between L5 and S1, into which implants are secured. The SEC can be used at any spinal level the surgeon deems in need of fusion.

Referring to FIG. 1, vertebral segments or end plates are shown with an average 8 mm gap representing an average intervertebral space. A complete discectomy is performed prior to the insertion of the SEC 100. The intervertebral disc occupying space 102 is removed using standard techniques including rongeur, curettage, and endplate preparation to bleeding subcondral bone. The posterior longitudinal ligament is divided to permit expansion of the intervertebral space.

The intervertebral space 102 is distracted to about 10 mm using a rotating spatula (Not shown. This is a well-known device that looks like a wide screw driver that can be placed into the disc space horizontally and turned 90 degrees to separate the endplates).

Figure 2:
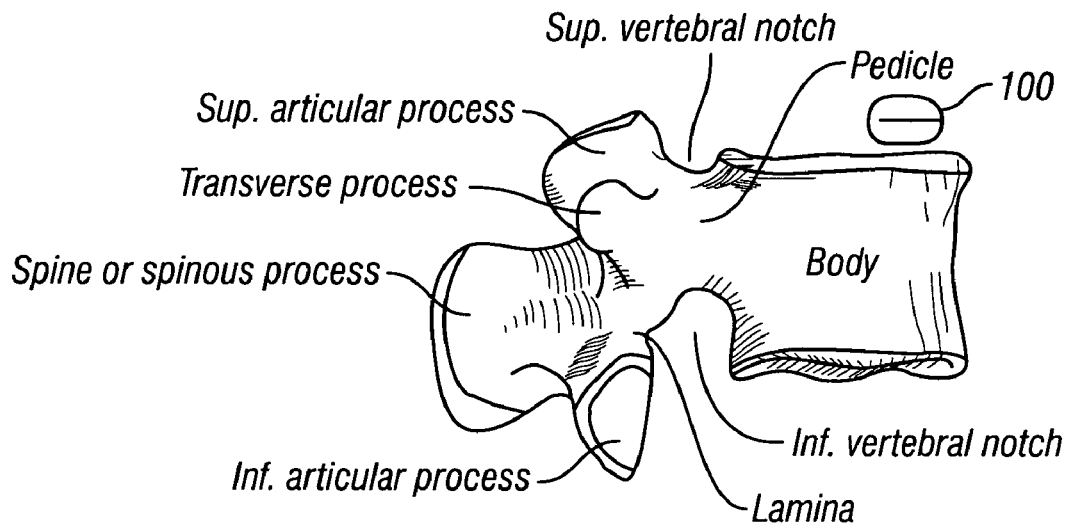
FIG. 2 is a side view of a vertebral body showing the placement of the SEC according to an aspect of the invention.
Figure 3:
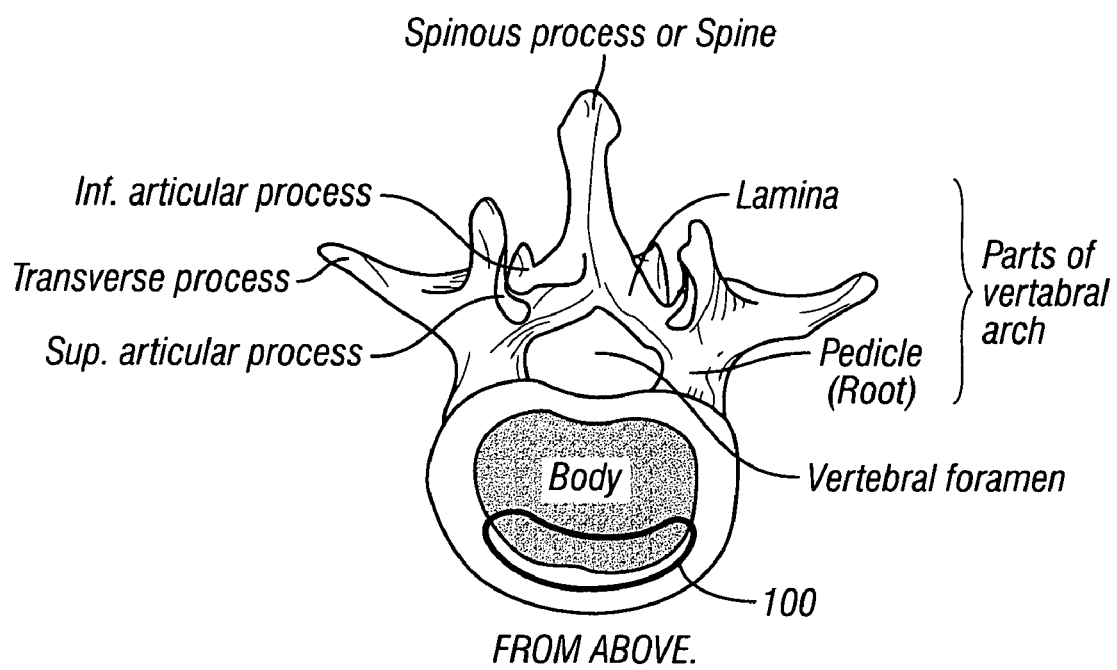
FIG. 3 is a top view of a vertebral body showing placement of the SEC according to an aspect of the invention.

The SEC is inserted posteriorly (in the direction of arrow 102 between the no. 4 and 5 lumbar vertebrae as shown in FIG. 1 (lateral view) or into any selected inververbral space. In accordance with an aspect of the invention, the SEC is reduced to small size in its unexpanded state to enable it to be inserted posteriorly through space 102 as shown in Figure. The dimensions of the SEC are: 12 mm wide, 10 mm high and 28 mm long to facilitate posterior insertion and thereby minimize trauma to the patient and risk of injury to nerve roots. Once in place the SEC can expand to 16 mm, or 160 percent of its unexpanded size, enabling 20 degrees or more of spinal correction medial and lateral. FIGS. 2 and 3 are a side view and top view, respectively showing the placement of the SEC 100 on a vertebral body.

Figure 4A:
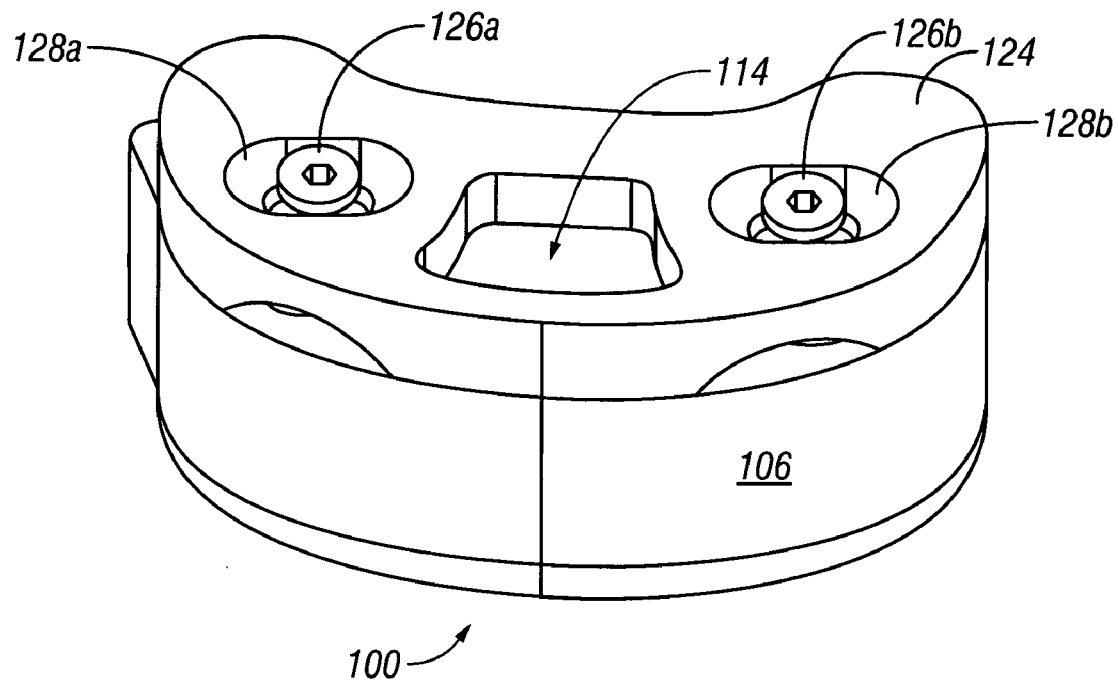
FIG. 4A is a front perspective view of the SEC in an unexpanded state according to an aspect of the invention.
Figure 4B:
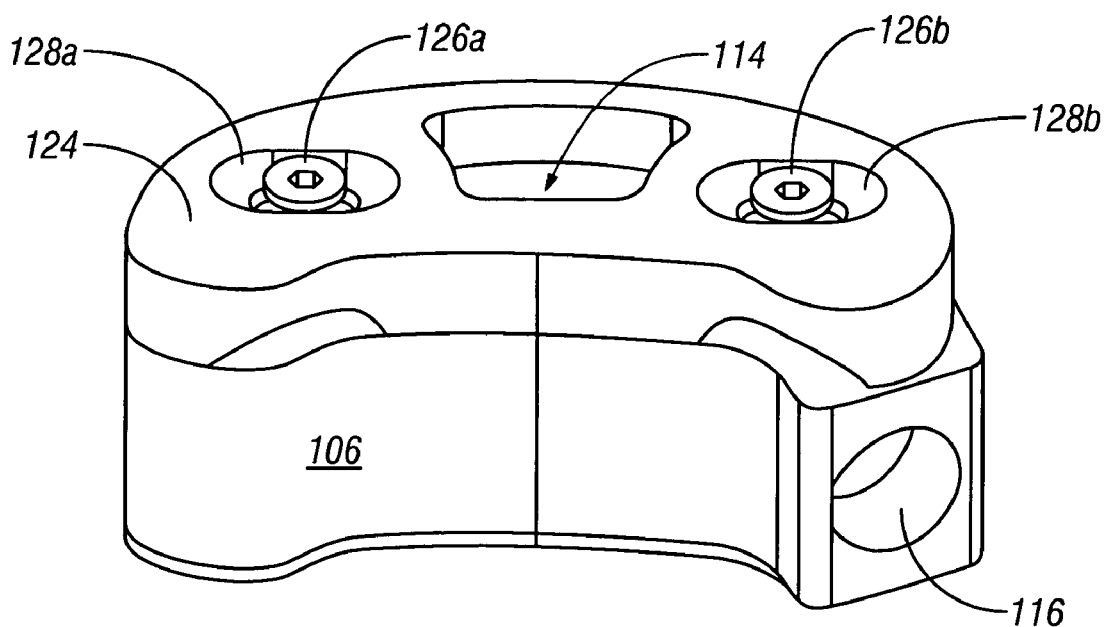
FIG. 4B is a rear perspective view of the SEC of FIG. 4A according to an aspect of the invention.

FIG. 4A shows SEC 100 from the front or anterior position with respect to the vertebral column. The SEC is shown in a closed or unexpanded position. Referring to FIGS. 4A through 4E, SEC 100 comprises a body or block 106 that defines one or more slave cylinders 108a, 108b (best seen in FIG. 5A) for corresponding pistons 110a, 110b. Pistons are provided with O rings 112a, 112b for a tight seal with the cylinder. Block 106 also defines a central cavity 114 for infusion of bone graft material into the intervertebral space when the SEC is fully expanded or during the expansion process, as will be explained.

Figure 4C:
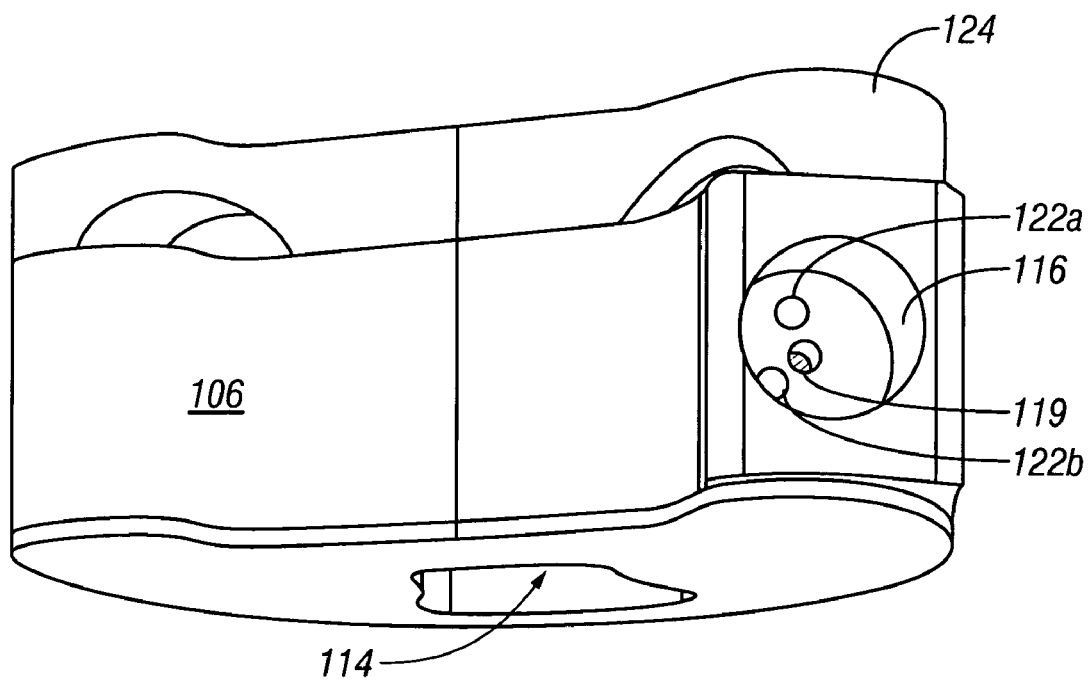
FIG. 4C is a rear perspective view of the SEC of FIG. 4A showing details of the hydraulic and bone graft input ports according to an aspect of the invention.
Figure 4D:
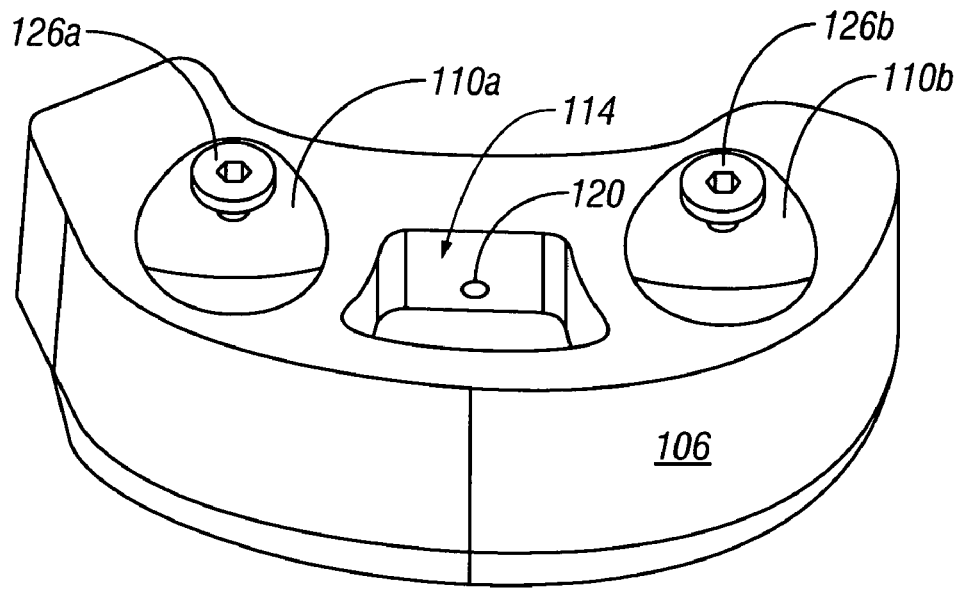
FIG. 4D is a perspective view of the SEC of FIG. 4A with the wedge plate removed for clarity.
Figure 4E:
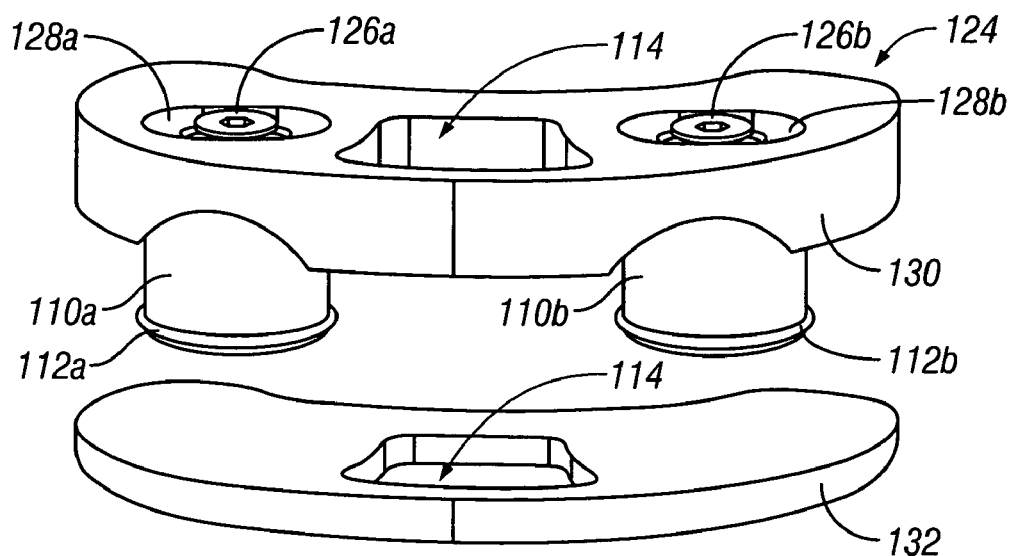
FIG. 4E is a perspective view of FIG. 4A showing the cylinders and bone graft perfusing cavity defined by the SEC body according to an aspect of the invention.
Figure 5A:
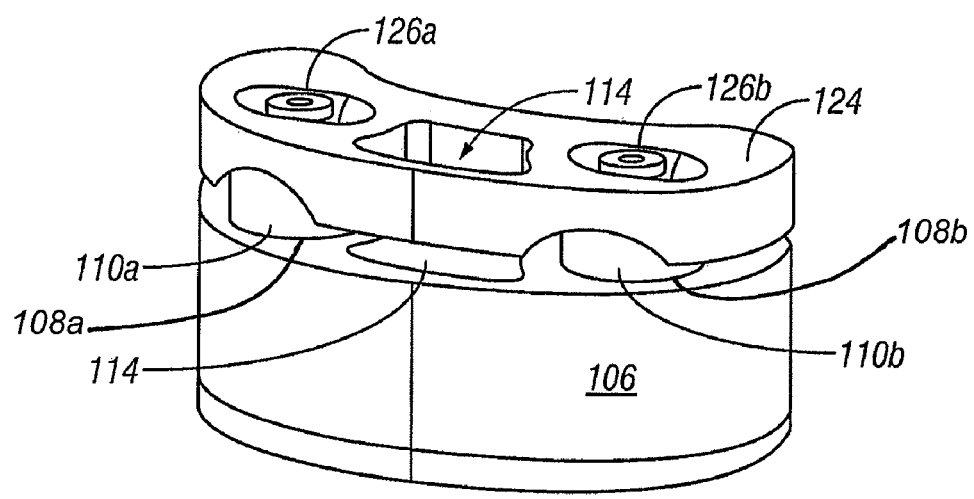
FIG. 5A is a front perspective view of the SEC in an expanded state according to an aspect of the invention.
Figure 5B:
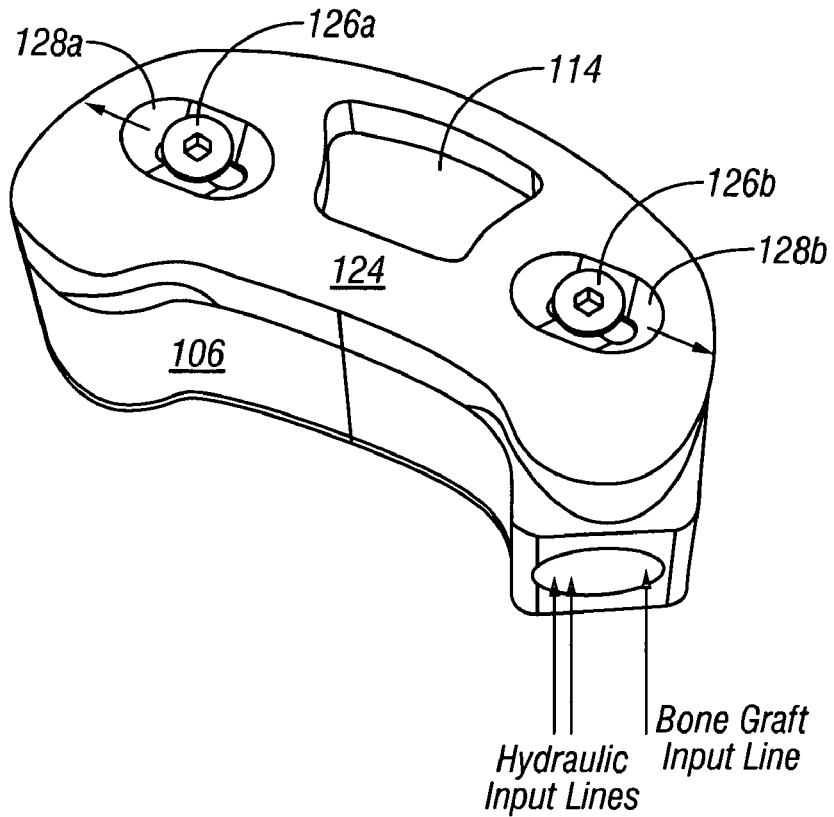
FIG. 5B is a top perspective view of the SEC showing the cavity for bone graft perfusion and recesses allowing lateral movement of the wedge according to an aspect of the invention.
Figure 5C:
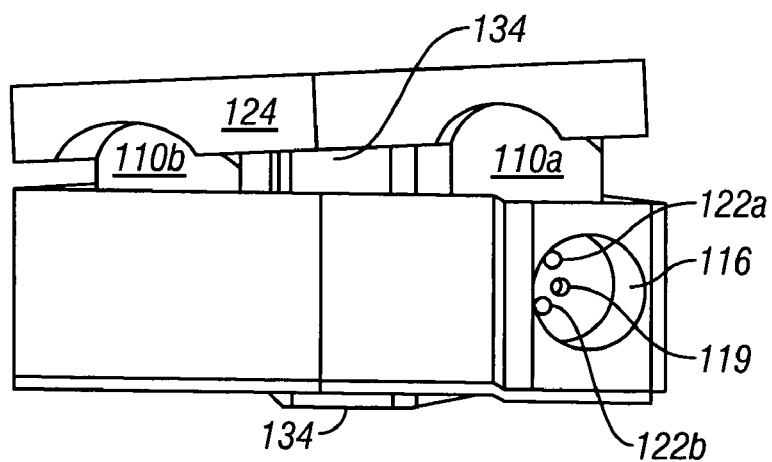
FIG. 5C is a rear perspective view of the SEC in an expanded state according to an aspect of the invention.
Figure 5D:
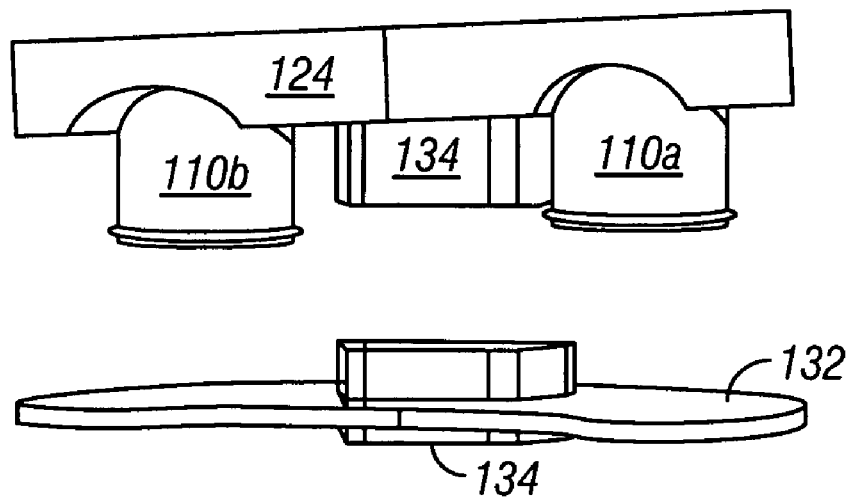
FIG. 5D is a perspective view of FIG. 5C with the SEC body removed for clarity.

As shown in FIG. 4C, block 106 further defines a central or main input port 116 for attachment of hydraulic lines and a line for transmission of a slurry or liquid bone graft material as will be explained. The block 106 defines a bone graft infusion conduit that extends from a bone graft input port 119 located in main input port 116 to a bone graft exit port 120 (see FIG. 4D) located in central cavity 114 for infusion of bone graft material therein.

Block 106 further defines local hydraulic fluid input ports 122a, 122b (FIG. 4C) that lead to corresponding slave cylinders 108a, 108b for driving the pistons and expanding the SEC by remote control from a master cylinder located ex vivo and with greatly increased force as compared to conventional devices.

It will be appreciated that each slave piston 110a, 110b is independently controlled by a separate hydraulic line 122a, 122b connected to a master cylinder (as will be explained with reference to FIGS. 7a through 8) located away from the patient and the site of implantation, thus minimizing active intervention by surgical tools in the immediate vicinity of nerve roots. Although two slave cylinders are shown by way of example, it will be appreciated that the invention is not so limited, but on the contrary, SEC block 106 easily is modifiable to define a multiplicity of slave cylinders, each controlled independently by a separate hydraulic line, for expanding differentially to provide a substantially infinite variety of space sensitive adjustments for unique applications.

Referring again to FIGS. 4A through 4G, an anterior/posterior corrective plate or wedge plate 124 is movably held in captured engagement on top of pistons 110a, 110b by corresponding hold down screws 126a, and 126b. Plate 124 enables spinal correction in the anterior/posterior direction as the cylinders expand vertically. Plate 124 has a bone-engaging top surface provided with two elongated slots 128a, 128b in which the hold down screws sit. The elongated slots 128*a*, 128*b* enable ease of expansion and facilitate angles between the pistons by allowing the plate 124 to move laterally slightly as pistons differentially expand. The plate also defines cavity 114 for the infusion of bone graft material, that is co-extensive with and the same as cavity 114 defined by the SEC block. This enables perfusion of the bone graft material directly through the bone engaging surface of the wedge plate into the adjacent vertebral body.

Figure 4F:
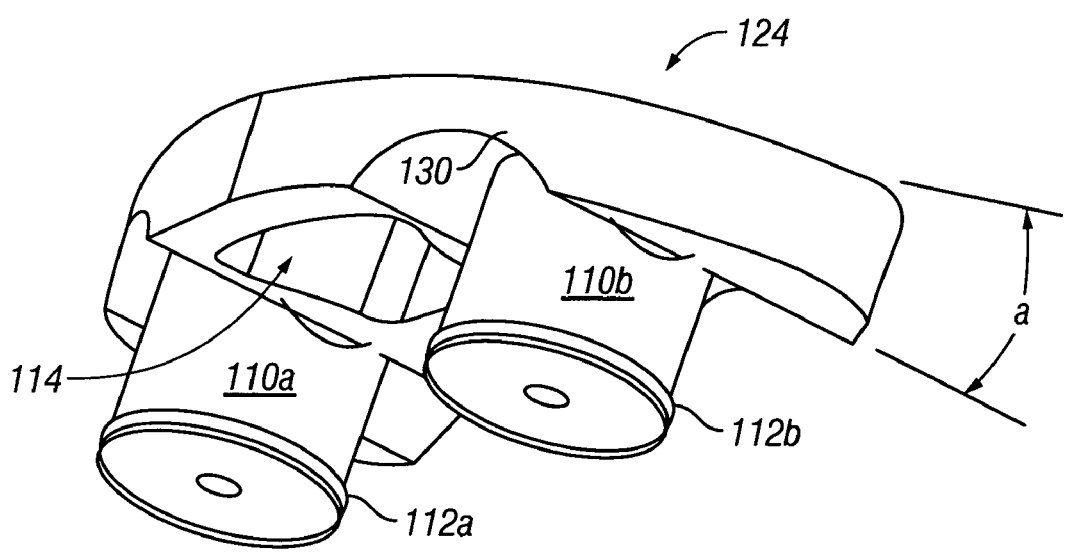
FIG. 4F shows another view of the wedge plate according to an aspect of the invention.
Figure 4G:
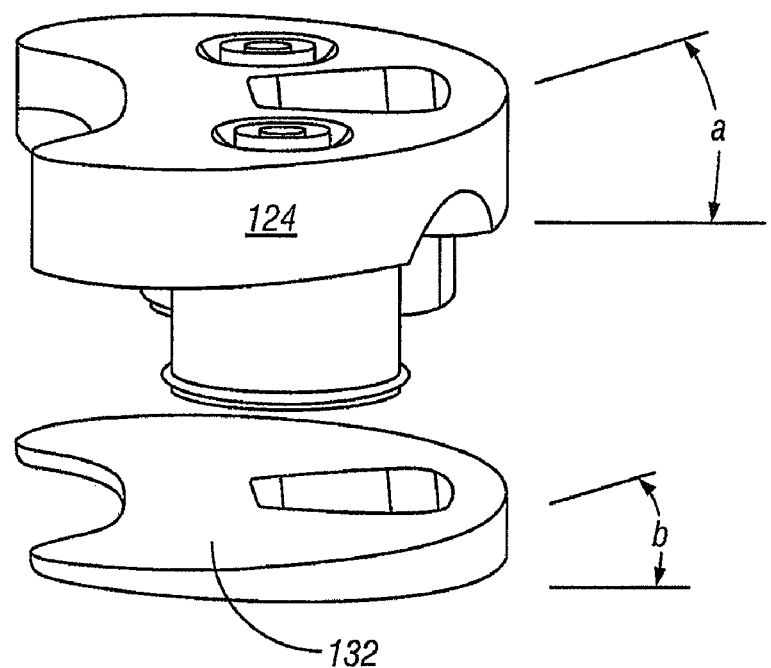
FIG. 4G shows details of the wedge plate and lordosis plate according to an aspect of the invention.

Referring to FIGS. 4F and 4G, the anterior/posterior corrective plate 124 is provided with a downwardly extending edge 130 for engagement with the pistons as they differentially expand, to ensure that wedge plate stays firmly in place. Plate 124 provides anterior/posterior correction in that it can be angled front to back like a wedge with a correction angle a of 0-5 degrees or more. Plate 124 also defines bone graft cavity 114 for enabling bone growth conductive or inductive agents to communicate directly with the engaged vertebral endplate.

The SEC is optionally provided with a lordosis base plate 132 that includes a bone engaging surface defining a cavity co-extensive with bone graft cavity 114 for enabling perfusion of bone graft material into the adjacent engaged vertebral body. Lordosis base plate also has an anterior/posterior angle b (refer to FIG. 6) of 0-5 degrees for correcting lordosis.

Referring to FIG. 4G, top plate 124 and optional lordosis base plate 132 function as two endplates providing a corrective surface that impacts vertebral bodies for spinal correction. Lordosis base plate 132 includes a bone-engaging surface defining a cavity co-extensive with bone graft cavity 114 for enabling perfusion of bone graft material into the adjacent opposed vertebral body. Lordosis base plate also has anterior/posterior angle b of 0-5 degrees for correcting lordosis. Thus, the wedge plate and lordosis base plate can provide lordotic correction of 10 degrees or more.

Surgeon control over sagittal alignment is provided by differential wedge shaping of the endplates and by calculated degrees of variable piston expansion. The endplates will be constructed with 0 degrees of wedge angle anterior to posterior, or 5 degrees. Therefore, the final construct may have parallel endplates (two 0 degree endplates), 5 degrees of lordosis (one 5 degree and one 0 degree endplate), or 10 degrees of lordosis (two 5 degree implants). This implant permits unprecedented flexibility in controlling spinal alignment in the coronal and sagittal planes.

Since vertebral end plates are held together at one end by a ligament much like a clamshell, expansion of the pistons vertically against the end plates can be adjusted to create the desired anterior/posterior correction angle. Thus, the top plate 124 does not need to be configured as a wedge. Where an extreme anterior/posterior correction angle is desired, the top plate and/or base plate may be angled as a wedge with the corresponding correction angles set forth above.

FIGS. 5A through 5D show the SEC in its expanded state. Hydraulic fluid flows from a master cylinder (FIG. 7A) into the cylinders through separate hydraulic input lines that attach to hydraulic input ports 122*a*, 122*b*. Each hydraulic line is regulated independently thereby allowing a different quantity of material to fill each cylinder and piston cavity pushing the pistons and medial/lateral wedge plate upward to a desired height for effecting spinal correction.

In accordance with an aspect of the invention, the hydraulic fluid communicating the mechanical leverage from the master cylinder to the slave cylinder or syringe and pistons advantageously is a time-controlled curable polymer such as methylmethacrylate. The viscosity and curing time can be adjusted by the formulation of an appropriate added catalyst as is well known. Such catalysts are available from LOCTITE Corp., 1001 Trout Brook Crossing, Rocky Hill Conn. 06067. When the polymer cures, it hardens and locks the pistons and thus the desired amount of spinal correction determined by the physician immovably in place.

It will be appreciated that the cylinder block 106 and pistons 110*a*, 110*b*, comprise a biocompatible, substantially incompressible material such as titanium, and preferably type 6-4 titanium alloy. Cylinder block 106 and pistons 110*a*, 110*b* completely confine the curable polymer that is acting as the hydraulic fluid for elevating the pistons. When the desired spinal correction is achieved by the expanded pistons, the curable polymer solidifies, locking the proper spinal alignment substantially invariantly in place. The confinement of the polymer by the titanium pistons and cylinder block provides the advantage of making the polymer and the desired amount of spinal alignment substantially impervious to shear and compressive forces.

For example, even if it were possible to compress the polymer it could only be compressed to the structural limit of the confining cylinder block. That is, by placing the curable polymer into the 6-4 titanium cylinder block wherein two or more cylinders are expanded, the polymer becomes essentially non-compressible especially in a lateral direction. It will be appreciated that 6-4 titanium cylinder block confining the hydraulic material provides extreme stability and resistance to lateral forces as compared to a conventional expanding implant. Further, there is no deterioration of the curable polymer over time in term of its structural integrity because it is confined in the titanium alloy body.

The use of the present 6-4 titanium cylinder block configuration can withstand compressive forces in excess of 12,000 Newtons or approx 3000 pounds of compressive force on the vertebrae. This is not possible in a conventional expanding structure wherein the expanding polymer is not confined by an essentially incompressible titanium body.

In accordance with another aspect of the invention, injectable bone graft material 134 is provided along a separate bone graft input line to bone graft input port 119 for infusion into cavity 114 through bone graft exit port 120.

The bone graft input line is controlled at the master cylinder or from a separate source to enable a pressure induced infusion of bone graft material 134 through cavity 114 of the bone engaging surfaces of the SEC into adjacent vertebral bone. Thus, the bone graft material fills, under pressure, the post-expansion space between adjacent vertebral bodies. This achieves substantially complete perfusion of osteo-inductive and/or osteo-conductive bone graft material in the post expansion space between the vertebral bodies resulting in enhanced fusion (refer to FIGS. 5C, 5D).

Minimally Invasive, Hydraulically Controlled Manipulation in Three Dimensions

Figure 6:
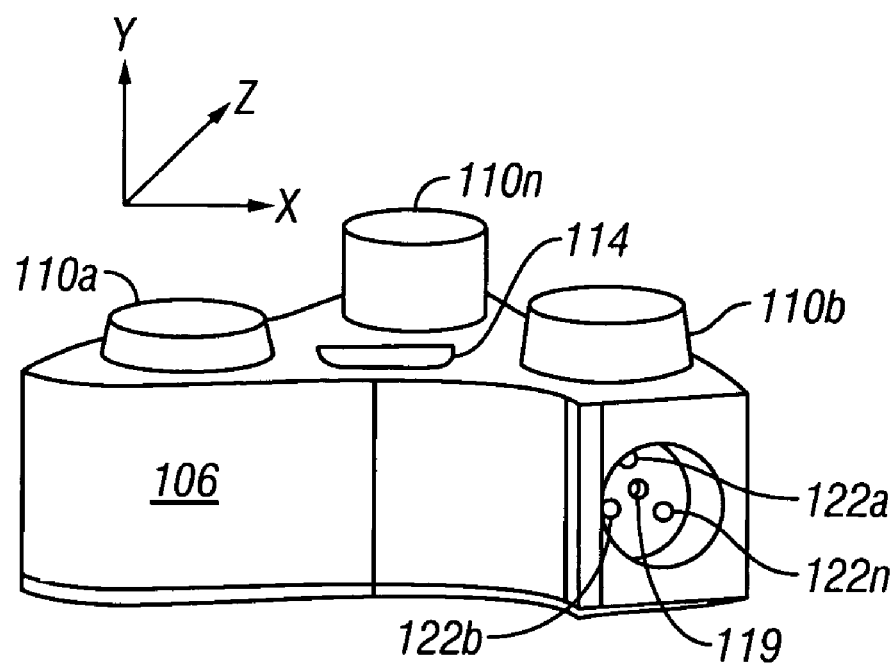
FIG. 6 is a perspective view of an alternate embodiment of the SEC according to an aspect of the invention.

Referring to FIG. 6, an alternate embodiment of the SEC comprises multiple slave cylinders and corresponding pistons 110*a*, 110*b*, 110*n* are provided in SEC body 106. Each of the multiple slave cylinders and pistons 110*a*, 110*b*, 110*n* is provided with a separate, associated hydraulic line 122*a*, 122*b*, 122*n* that communicates independently with a corresponding one of a plurality of cylinders in the master cylinder for independently controlled expansion of the slave cylinders at multiple elevations in three dimensions (X, Y and Z axes).

At the master cylinder, multiple threaded cylinders (or disposable syringes) and pistons are provided, each communicating independently through a separate hydraulic line 122*a*, 122*b*, 122*n* with a corresponding one of the slave cylinders and pistons 110*a*, 110*b*, 110*n* in the LEC.

The bone engaging surfaces of the multiple pistons 110a, 110b, 110n provide the corrective surface of the SEC. Thus, by appropriate adjustment of the pistons in the master cylinder, or depending on fluid installed via separate syringes, the surgeon can independently control expansion of the slave pistons in the SEC to achieve multiple elevations in three dimensions for specialized corrective applications. A top or wedge plate is not necessary.

The bone engaging surface 111 of the slave pistons 110a, 110b, 110n in the LEC may be provided with a specialized coating for bone ingrowth such as hydroxyapetite. Alternatively, the bone-engaging surface 111 of the SEC pistons may be corrugated, or otherwise provided with a series of bone engaging projections or cavities to enhance fusion.

As previously explained, the hydraulic fluid communicating the mechanical leverage from the master cylinder to the SEC slave cylinders and pistons 110a, 110b, 110n is a time-controlled curable polymer such as methylmethacrylate that locks the SEC immovably in place after curing, at the desired three dimensional expansion.

As set forth above, injectable bone graft material is provided along a separate bone graft input line to bone graft input port 119 for infusion into cavity 114 through into the inter body space between the SEC and adjacent bone.

The surgeon by adjustment of the master cylinder is able to provide remotely a controlled angle of the SEC corrective surface to the medial/lateral (X axis) and in the anterior, posterior direction (Z axis). The surgeon also can adjust the SEC in the vertical plane moving superiorly/inferiorly (Y axis) from the master cylinder or power/flow source to control implant height. Thus, three-dimensional control is achieved remotely through a hydraulic line with minimal trauma to a patient. This aspect of the invention advantageously obviates the need to manually manipulate the SEC implant at the site of intervention to achieve desired angles of expansion. Such conventional manual manipulation with surgical tools into the intervention site can require further distracting of nerve roots and cause potential serious trauma to a patient.

Figure 7A:
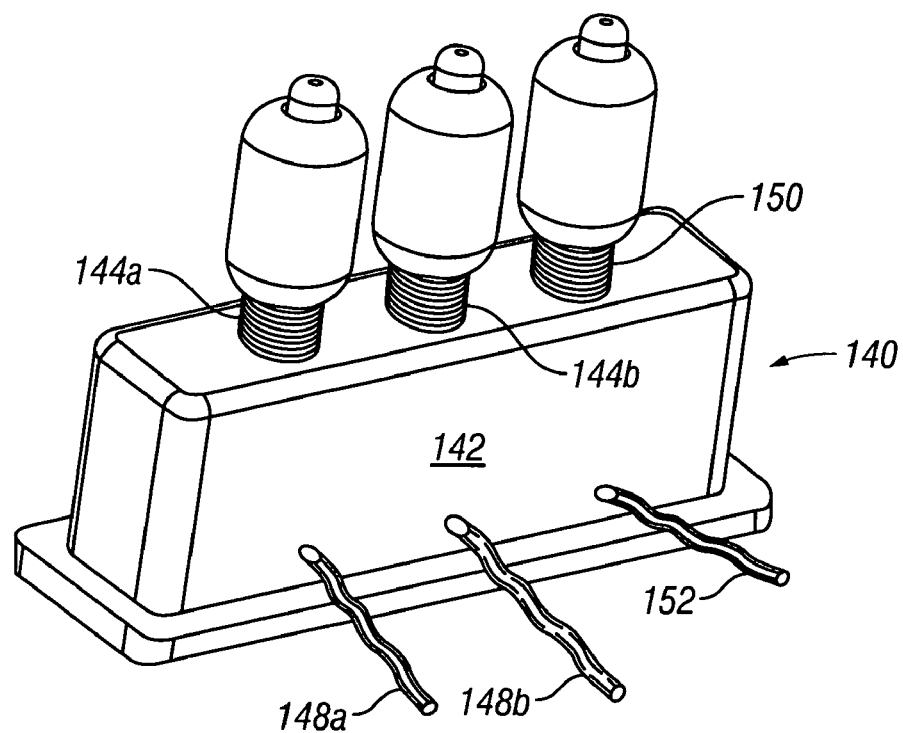
FIG. 7A is a perspective view of a master cylinder for hydraulic control of the SEC according to an aspect of the invention. A variety of alternative embodiments are available, most simply disposable syringes used for piston expansion.
Figure 7B:
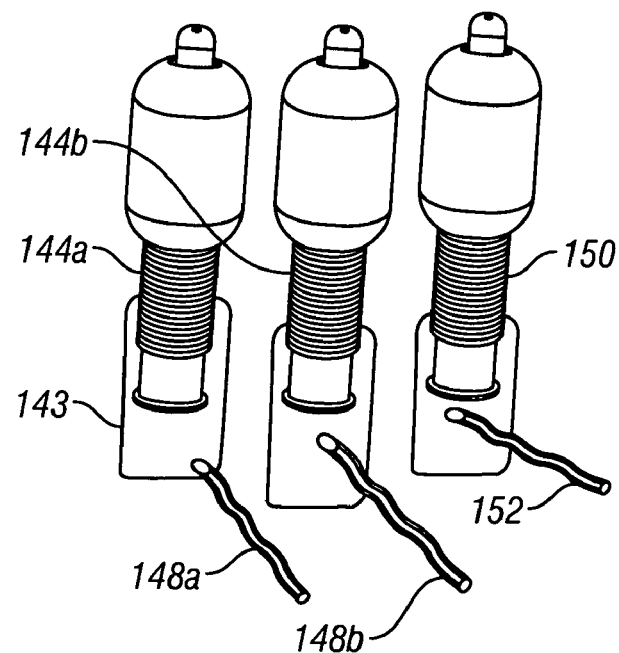
FIG. 7B is a view of the interior of FIG. 7A.

Referring to FIGS. 7A and 7B, in accordance with an aspect of the invention, a master cylinder 140 located remotely from the patient, provides controlled manipulation and adjustment of the SEC in three dimensions through independent hydraulic control of slave cylinders 110a, 110b in the SEC. Master cylinder 140 comprises a cylinder block 142, defining two or more threaded cylinders 143. Corresponding screw down threaded pistons are rotated downward into the threaded cylinders thereby applying force to a hydraulic fluid in corresponding hydraulic control lines that communicate independently with and activate corresponding slave cylinders 110a, 110b in the SEC with mechanical leverage. The rotational force for applying the mechanical leverage at the slave cylinders is controlled by thread pitch of the threaded pistons in the master cylinder, or in an alternate embodiment controlled by use of syringes, one acting as a master cylinders for each piston or slave cylinder to modulate piston elevation.

In FIG. 7B threaded pistons 144a, 144b are provided in hydraulic cylinders communicating through hydraulic lines 14ba, 148b that are coupled to hydraulic input ports 116a, 116b for independent hydraulic control of slave cylinders 110a, 110b as previously explained.

Another threaded cylinder and piston assembly 150 is supplied with a quantity of bone graft material in slurry or liquid form and operates in the same way to provide the bone graft material under pressure to the SEC bone graft input port 119 through bone graft supply line 152. Thus, bone graft material is forced under pressure from the master cylinder through cavity 114 and into the intervertebral space.

Alternate Master Cylinder System

Figure 8:
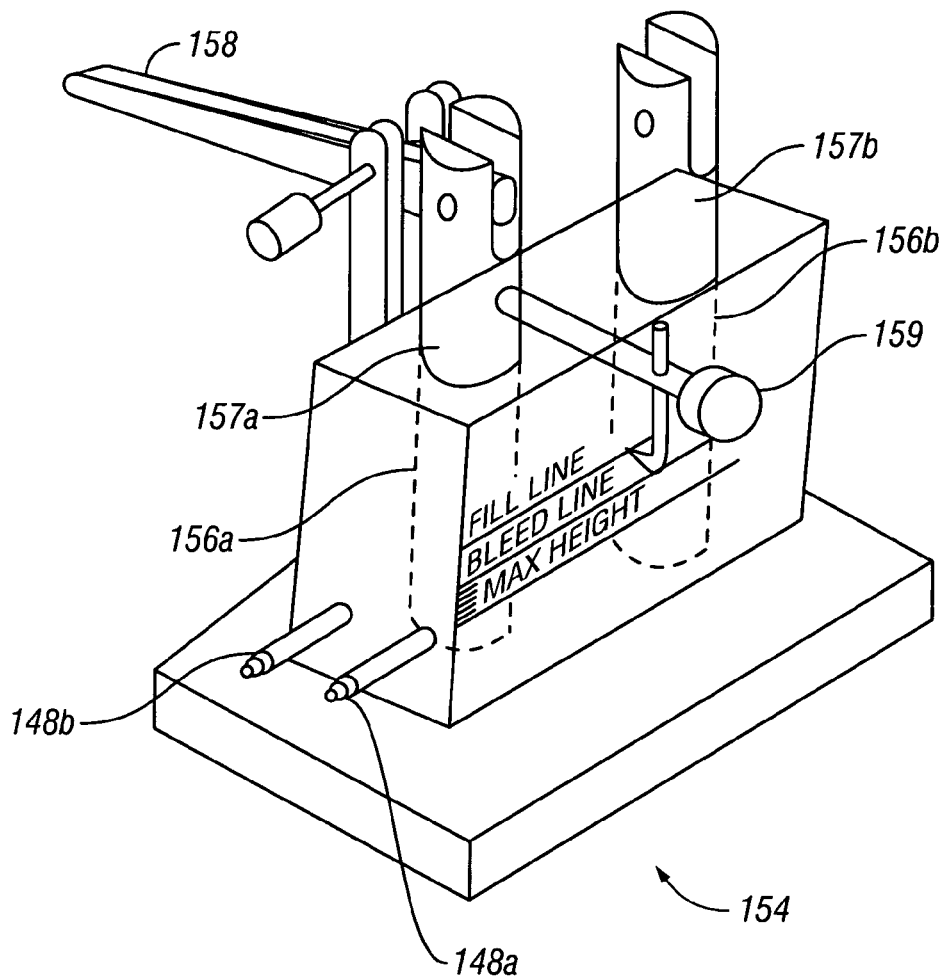
FIG. 8 is a perspective view of an alternate embodiment of the master cylinder according to an aspect of the invention.

Referring to FIG. 8, an alternate embodiment of a master cylinder is provided for individual hydraulic control of each slave piston in the SEC implant. A master cylinder 154 is provided with two or more cylinders 156a, 156b, and associated pistons 157a, 157b. A lever 158 controlled by the surgeon is attached to each piston. Hydraulic fluid feeds through lines 148a 148b into the inserted SEC implant. The lever creates a ratio of 1 pound to 10 pounds of pressure inside the slave cylinders in the SEC and thus against vertebral endplates. Mechanically this provides a 10:1 advantage in lift force for the surgeon. The surgeon's required force application is multiplied via the lever and hydraulic system to create a controlled expansion of the SEC against the endplates as previously described to create any desired spine vertebral correctional effect in three dimensions.

If the surgeon uses one pound of force on the lever, the piston exerts 10 pounds of force. The piston in the master cylinder displaces the hydraulic fluid through hydraulic lines 148a, 148b. The hydraulic lines are flexible conduit no more than 3 mm in diameter. Thin hydraulic lines are desirable to increase mechanical advantage at the slave cylinders in the SEC. If one pound of pressure is exerted on the handle, the corresponding piston in the SEC would have 10 pounds of lifting force. If each slave piston inside the SEC implant has 200 pounds of lifting force, the required amount of pressure applied by the surgeon to the master piston cylinder is 20 pounds, or one tenth the amount, consistent with the predetermined mechanical advantage.

In usual cases, where the surgeon has a patient in a partially distracted anatomic, anesthetized and relaxed position under anesthesia, 30 pounds of force may be required for implant expansion upon the vertebral bone endplates. The surgeon in that case would need to apply only 3 pounds of pressure to lever 158. Different ratios may be introduced to optimize distraction force while minimizing injection pressures.

The pressure application process is guided by normal surgical principles, by visual checkpoints, and by a safety gauge that illustrates the amount of expansion that has been exerted in direct correlation with the implant expansion process. The gauge indicates the height of the slave pistons and thus the vertical and angular expansion of the SEC. This translates to an ability to clarify the percentage of lateral expansion. That is, if the surgeon chooses to create an angle, he expands the right slave cylinder, for example, 14 mm and left slave cylinder 12 mm.

The master cylinder 154 preferably comprises transparent plastic to enable visual indication of the height of the hydraulic fluid therein, or a translucent plastic syringe to facilitate exact measured infusion of the slave cylinder implant expanding pistons. A knob 159 for setting gauge height is provided in each cylinder. An indicator attached to the knob registers the cylinder height with respect to a fill line, bleed line or maximum height line. The master cylinder and slave cylinders are filled with hydraulic fluid. Air is removed by bleeding the cylinders in a well-known manner. The knob indicator is registered to the bleed line. A series of incremental marks are provided between the bleed line and the maximum height line to show the surgeon the exact height of the slave cylinder in response to the surgeon's control inputs to the master cylinder.

It will be appreciated that the master and slave hydraulic system interaction can have many equivalent variations. For example, the master cylinder function of master cylinder 154 also can be provided by one or more syringes. Each syringe acts as a master cylinder and is coupled independently with a corresponding slave cylinder through a thin hydraulic line for independent activation as previously described. A single syringe acting as a master cylinder also may be selectively coupled with one or more slave cylinders for independent activation of the slave cylinders. As is well known, series of gradations are provided along the length of the syringe that are calibrated to enable the surgeon to effect a precise elevation of a selected piston at the corresponding slave cylinder in the implant.

As previously explained, the SEC implant also expands vertically the intervertebral space from 10 mm to 16 mm or more. Additionally, by changing the diameter of the piston inside the master cylinder, the force exerted into the slave cylinder could be multiplied many fold so as to create major force differentials. The foregoing features provide the surgeon with an ability to establish a spinal correction system that is a function of the needed change to correct a deformity, so as to produce normal alignment.

Figure 9A:
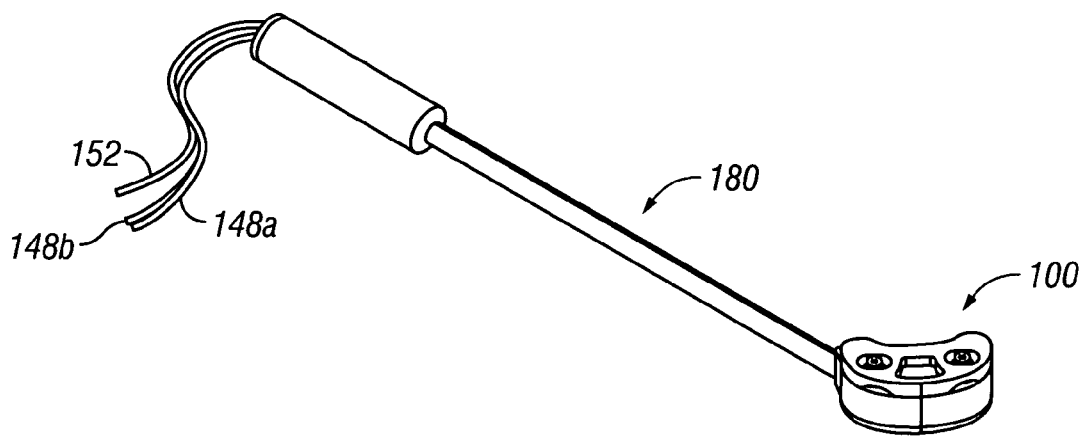
FIG. 9A is a perspective view of the insertion tool holding the SEC, hydraulic lines and bone graft supply line according to an aspect of the invention.
Figure 9B:
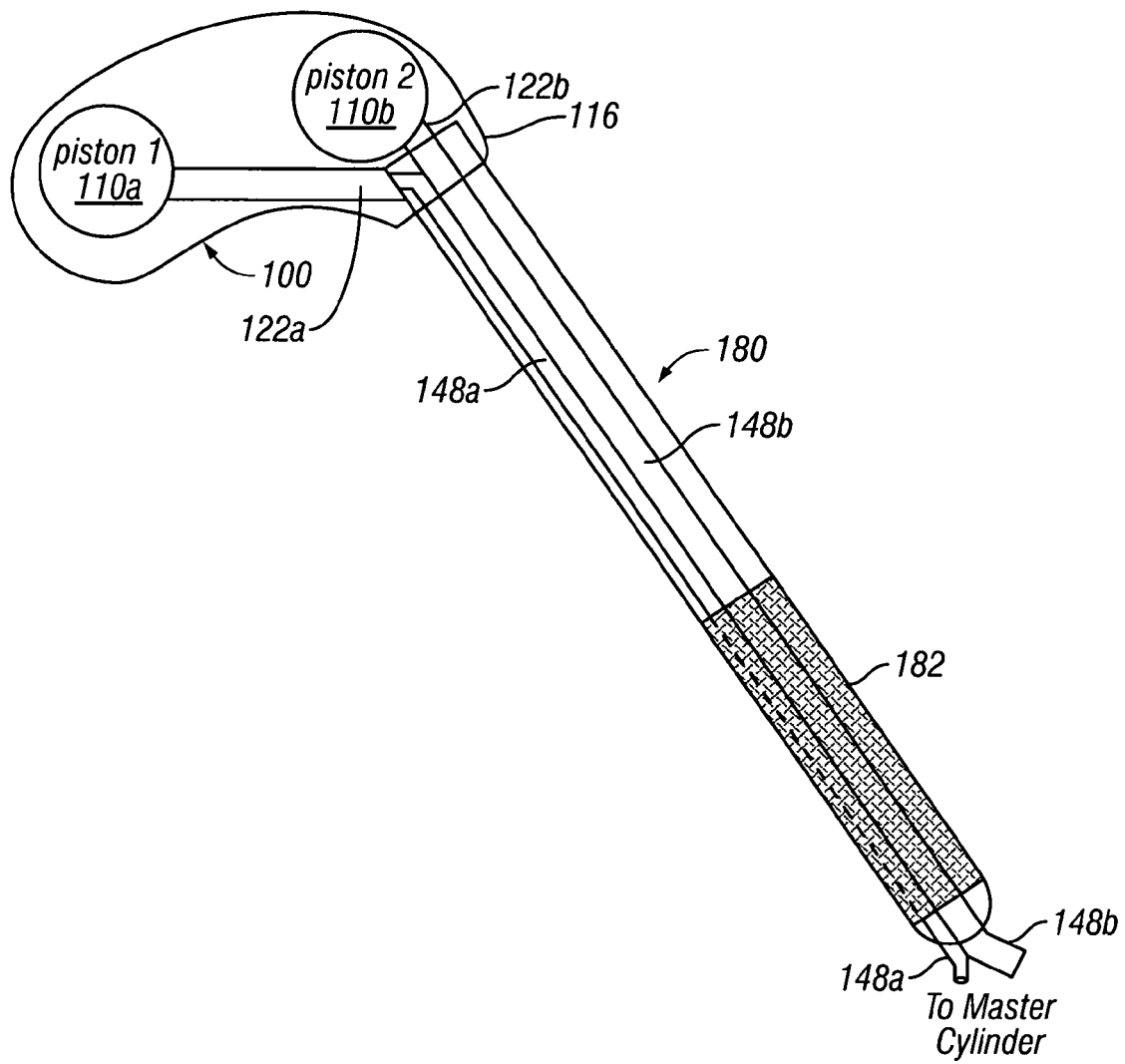
FIG. 9B is a close up view of the insertion tool of FIG. 9A.

Referring to FIG. 9A, it will be appreciated that hydraulic control lines 148 and bone graft supply line 152 are characterized by a minimal size and are provided in the interior of a very narrow insertion tool 180 (FIGS. 9A and 9B). The insertion tool 180 is small enough to insert the SEC 100 posteriorly into the narrow insertion opening without risk of serious trauma to the patient. An enlarged view of the insertion tool 180 (simplified for clarity) is shown in FIG. 9B. The insertion tool 180 includes a handle 182 and hollow interior for housing hydraulic control lines and a bone graft supply line (not shown for clarity). The hydraulic control lines and bone graft supply line connect through a proximal end of the insertion tool to the master cylinder. A distal or insertion end of the tool holds the SEC 100. In a preferred mode, the insertion end of the insertion tool conformably fits in the SEC hydraulic input port 116. Hydraulic control lines and the bone graft supply line are connected to the hydraulic input ports 122a, 122b and bone graft supply input port respectively, prior to surgery.

The bone graft supply and hydraulic control lines are safely retracted after the SEC is positioned. The hydraulic lines can be released by cutting after the operation since the hydraulic fluid hardens in place.

When the SEC is locked in position by the surgeon, the insertion tool and hydraulic tubes are removed and the curable polymer remains in the SEC slave cylinders.

In accordance with an aspect of the invention, the hydraulic fluid controlling the movement of the SEC is a time-controlled curable polymer that hardens after a pre-determined time period, locking the SEC insert immovably in a desired expanded position. The hydraulic fluid is preferably methylmethacrylate or other similar inexpensive polymer, with a time controlled curing rate. Time-controlled curable polymers typically comprise a catalyst and a polymer. The catalyst can be formulated in a well-known manner to determine the time at which the polymer solidifies. Such time-controlled curable polymers are commercially available from several manufacturers such as LOCTITE Corp., Henkel-Loctite, 1001 Trout Brook Crossing Rocky Hill, Conn. 06067.

Light Curable Polymer

As is well understood by one skilled in the art, any equivalent curable polymer that has a first flowable state for conveying hydraulic force, and that transitions to a second solid state upon curing may be employed. In the first state, the curable polymer transfers the application of force hydraulically from the master cylinder to the slave cylinders, such that corrective action is achieved by elevating the slave pistons. The curable polymer transitions to a second solid state upon curing such that the corrective elevation of the slave pistons is locked in place. Such an equivalent curable polymer is a polymer that is cured through the application of either visible or ultraviolet light or other radiation source which activates the polymer to transition to a solid state. Another methylmethacrylate liquid polymer when combined with powder becomes a viscous fluid as soon as the powder and liquid are blended; it is initially thin and free flowing. Gradually, in minutes, it begins to thicken, transforming state through paste and puddy to cement-like solid once inside the pistons, thus fixing the SEC at a precise correction amount in its expanded position.

An example of such a light curable polymer is UV10LC-12 made by MASTER BOND Inc., of Hackensack, N.J. Such polymers are characterized by a fast cure time cure upon exposure to a visible or a UV light source. Depending upon the intensity of the light source, cure times range from a few seconds to less than a minute. As is well understood by one skilled in the art, an extremely thin fiber optic line may be incorporated as an additional line along with the multiple hydraulic lines shown in Figure for conveying light from a light source directly to the polymer in the slave cylinders to effect curing.

Alternatively, a curable polymer may be activated by a radiation source such as low level electron beam radiation to cure or initiate curing. An electron beam advantageously can penetrate through material that is opaque to UV light and can be applied directly to lock the pistons in their elevated or corrective position.

It will be appreciated that the amount of applied stress required to cause failure of the corrective implant is substantial due to the confinement of the cured polymer completely within the body of the implant, that is, the cylinder block that is comprised of 6-4 titanium. This is particularly advantageous since the confinement within the titanium body enables the corrective position of the implant to withstand compressive forces up to the structural failure limit of the titanium body; that is, to withstand compressive forces in a range of from 8000 up to 12,000 Newtons.

Hydraulic Control Lines

Figure 10A:
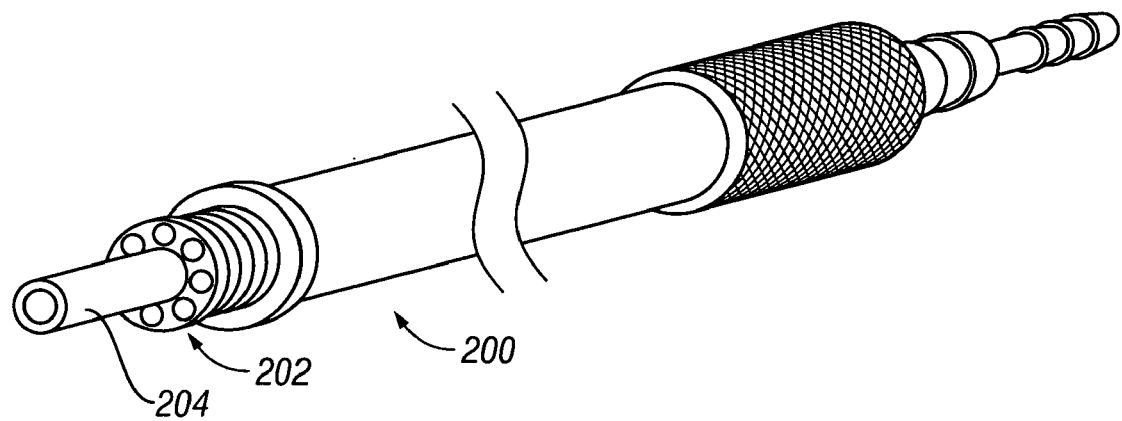
FIG. 10A shows one embodiment of a hydraulic line for independent control of multiple slave cylinders according to an aspect of the invention.
Figure 10B:
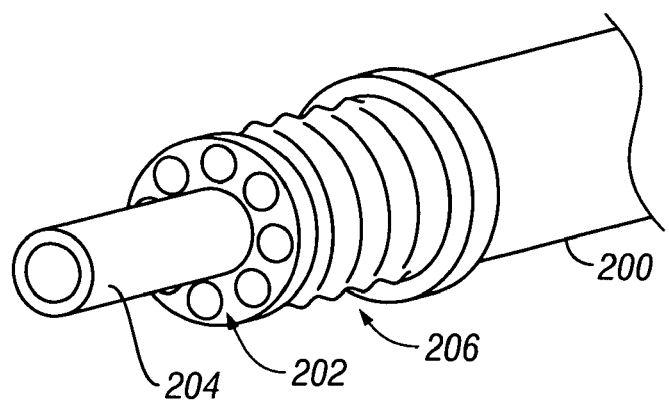
FIG. 10B shows a close up of the fitting for the hydraulic line of FIG. 10A according to an aspect of the invention.

Referring to FIGS. 10A and 10B, a hydraulic line 200 is provided for remote hydraulic control of a plurality of slave cylinders of the SEC from a master cylinder. Hydraulic line 200 comprises a plurality of individual hydraulic lines 202 disposed about a central axis. Each hydraulic line 202 provides independent activation of a separate slave cylinder from a master cylinder as previously explained. A bone graft supply line 204 is provided along the central axis of line 200. Individual hydraulic lines 202 can be aligned and connected with corresponding slave cylinder input ports prior to insertion of the SEC for providing independent hydraulic control to each of the slave cylinders. A threaded end 206 can be inserted into a similarly threaded central input port 116 of the SEC to prevent pull out.

In summary, remote hydraulic control of a spinal implant is particularly advantageous in a posterior insertion procedure because there is no anatomic room for mechanical linkage or tooling in the proximity of the adjacent spinal cord and neurovascular complex. The hydraulic control provided by the present invention provides significant mechanical leverage and thus increased force to an extent that has not previously been possible. Further, such hydraulic force is selective in both direction and magnitude of its application.

It is now possible to expand fenestrated endplates to support the anterior spinal column. This will create immediate and reliable firm fixation that will lead to immediate stabilization of the functional spinal motion segment, and immediate correction of complex interbody deformities in the sagittal and coronal plane.

The SEC provides advantages over currently existing technology that include correction of coronal plane deformity;

introduction of interbody lordosis and early stabilization of the interbody space with rigidity that is greater than present spacer devices. This early stability may improve post-operative pain, preclude the need for posterior implants including pedicle screws, and improve the rate of successful arthrodesis. Importantly, the SEC provides improvement of space available for the neural elements while improving lordosis. Traditional implants are limited to spacer effects, as passive fillers of the intervertebral disc locations awaiting eventual fusion if and when bone graft in and around the implant fuses. By expanding and 'morphing' into the calculated shape which physiologically corrects spine angulation, the SEC immediately fixes the spine in its proper, painless, functional position. As infused osteoinductive/osteoconductive bone graft materials heal, the patient becomes well and the implant becomes inert and quiescent, embedded in bone, and no longer needed.

While the invention has been described in connection with what are presently considered to be the most practical and preferred embodiments, it is to be understood that the invention is not limited to the disclosed embodiments and alternatives as set forth above, but on the contrary is intended to cover various modifications and equivalent arrangements included within the scope of the following claims.

For example, equivalent expansion surfaces can be provided for stabilizing the expanding SEC against the bone. Other compositions of additives may be used for the hydraulic fluid that achieves remote controlled expansion of the SEC in three dimensions. Similarly, various types of biogenic fluid material for enhancing bone growth may be injected through one or more lines to the SEC and different exit apertures may be provided to apply bone graft material to fill the intervertebral space, without departing from the scope of the invention.

Further, the invention can comprise a spinal implant that incorporates load or pressure sensors that register differential pressure and pressure intensity exerted on the back's engaging surface of the implant by the patient's vertebrae end plates to generate corrective signals, for example by computer control, that are used, e.g. by the surgeon or by a computer controlled mechanism to realign the patient's spine. The invention may further include a system that makes these adjustments, responsive to sensor signals, in real time and on a continual basis, such that the shapes of the implant changes to realign the patient's spine or mechanism. Preferably, such system is contemplated for use in setting the positions of the pistons during installation of the implant.

The invention also comprises the use of any of a solid or tubular coiled spring and a compressible fluid, e.g. a gas, such as air, in the cylinders to provide some movement of the implant plates to accommodate the patient's spinal movement. This embodiment provides a form of a shock absorber.

The implant itself can be made of, for example, such materials as titanium, 64 titanium, or an alloy thereof, 316 or 321 stainless steel, biodegradeable and biologically active materials, e.g. stem cells, and polymers, such as semi-crystalline, high purity polymers comprised of repeating monomers of two ether groups and a keytone group, e.g. polyaryetheretherketone (PEEK)™, or teflon.

Finally, the implant may provide two or more pistons that are operated concurrently to provide coordinated medial/lateral adjustment of a patient's spine for scoliosis, with anterior/posterior adjustment of the patient's spine to create natural lordosis, with relative anterior expansion greater than posterior expansion.

Therefore, persons of ordinary skill in this field are to understand that all such equivalent processes, arrangements and modifications are to be included within the scope of the following claims.

The invention claimed is:

1. A method for providing spinal correction, comprising:
   a. providing an interbody implant having
      i. a base comprising a cylinder block defining at least two cylinders and a first pressure applying, bone engaging surface;
      ii. first and second hydraulically actuatable pistons, one each extendably disposed in one said cylinder;
      iii. a pressure applying member having a second pressure applying, bone engaging surface coupled to at least one of the first and second pistons opposite the first bone engaging surface;
   b. removing at least part of a spinal disc between two of the patient's vertebral bodies;
   c. inserting the interbody implant between the two vertebral bodies with the first pressure applying surface of the base engaging a surface of one of the two vertebral bodies;
   d. hydraulically extending the pistons so that the pressure applying member coupled to at least one of the first and second extendable members engages a surface of the second vertebral body and supports the second engaged vertebral body in a desired position; and
   e. further comprising locking the pistons in an extended configuration.

2. The method of claim 1, wherein the first and second pistons are extendable independently to provide a desired spinal correction.

3. The method of claim 1, wherein the first and second pistons are extended by hydraulic actuation to distract the two vertebral bodies to provide a desired spinal correction.

4. The method of claim 1, wherein said hydraulically extending comprises delivering hydraulic fluid to said cylinders.

5. The method of claim 4 wherein the hydraulic fluid is a curable polymeric material.

6. The method of claim 5 wherein the curable polymeric material is methylmethacrylate.

7. The method of claim 5, wherein the polymeric material cures to a solid state to lock at least one of the first and second pistons in an extended configuration to provide a desired amount of spinal correction.

8. The method of claim 4, wherein the hydraulic fluid in an incompressible fluid.

9. The method of claim 1, wherein said locking in an extended configuration comprises curing a polymer within said cylinders.

10. The method of claim 1, wherein said cylinders are slave cylinders and said hydraulically extending comprises actuating a master cylinder located away from the patient and communicating hydraulically with each slave cylinder for operating a corresponding slave piston to impart a desired spinal correction.

11. The method of claim 1, wherein the locked extended pistons can withstand compressive forces up to a structural failure limit of the cylinder block.

12. The method of claim 1, wherein the locked extended pistons can withstand compressive forces in a range from 8000-12000 Newtons, or 3000 lbs.

13. The method of claim 1 wherein the pistons are locked in the extended configuration to maintain the desired spinal correction.

14. The method of claim 1, wherein the interbody implant has a maximum transverse dimension of about 0.8-1 cm in an unexpanded state to facilitate insertion to an intervertebral space.

15. A method for providing spinal correction, comprising:
   a. providing an interbody implant having
      i. a base including a first pressure applying, bone engaging surface;
      ii. first and second extendable members cooperating with the base;
      iii. a pressure applying member having a second pressure applying, bone engaging surface coupled to at least one of the first and second extendable members;
   b. removing at least part of a spinal disc between two of the patient's vertebral bodies;
   c. inserting the interbody implant between the two vertebral bodies with the first pressure applying surface of the base engaging a surface of one of the two vertebral bodies; and
   d. extending the first and second extendable members so that the pressure applying member coupled to at least one of the first and second extendable members engages a surface of the second vertebral body and supports the second engaged vertebral body in a desired position;
   wherein the extendable members are locked in the extended configuration to maintain the desired spinal correction; and
   wherein the extendable members are locked in the extended configuration by hydraulic fluid employed to extend the extendable members.

16. The method of claim 15 wherein the hydraulic fluid is a curable polymeric material and is cured to lock the extendable members in the extended configuration.

17. A method for providing spinal correction, comprising:
   a. providing an interbody implant having
      i. a base including a first pressure applying, bone engaging surface;
      ii. first and second extendable members cooperating with the base;
      iii. a pressure applying member having a second pressure applying, bone engaging surface coupled to at least one of the first and second extendable members;
   b. removing at least part of a spinal disc between two of the patient's vertebral bodies;
   c. inserting the interbody implant between the two vertebral bodies with the first pressure applying surface of the base engaging a surface of one of the two vertebral bodies; and
   d. extending the first and second extendable members so that the pressure applying member coupled to at least one of the first and second extendable members engages a surface of the second vertebral body and supports the second engaged vertebral body in a desired position;
   wherein bone graft material is provide through an aperture in the base member to facilitate infusion of bone graft material into an intervertebral space.

18. A method for providing spinal correction, comprising:
   a. providing an interbody implant having
      i. a base including a first bone engaging surface;
      ii. first and second extendable members cooperating with the base and defining a cavity therebetween opening through the base;
      iii. a pressure applying member having a second bone engaging surface coupled to at least one of the first and second extendable members;
   b. removing at least part of a spinal disc between two of the patient's vertebral bodies to form an intervertebral space;
   c. inserting the interbody implant into the intervertebral space with the first bone engaging surface of the base engaging a surface of one of the two vertebral bodies; and
   d. extending the first and second extendable members so that the second bone engaging engages a surface of the second vertebral body and supports the second engaged vertebral body in a desired position;
   e. disposing an osteoconductive material in said cavity between the two extendable members communicating with the intervertebral space.

19. The method of claim 18, wherein said disposing comprises infusing the osteoconductive material through a passageway formed in the interbody implant communicating with said cavity.

20. The method of claim 19, wherein said disposing takes place after said inserting.

21. A method for rigid fixation of spinal vertebrae, comprising:
   hydraulically distracting two opposed vertebral bodies, including placing at least one hydraulically extendable member between the two vertebral bodies, to position said bodies in a distracted location with respect to each other; and
   rigidly fixing the vertebral body in the distracted location;
   wherein said placing at least one hydraulically extendable member comprises
      removing at least part of a spinal disc between the two vertebral bodies; and
      inserting an implant between the two vertebral bodies, the implant comprising a base comprising a cylinder block defining at least two cylinders and a first bone engaging surface, at least two hydraulically actuatable pistons, one each extendably disposed within one said cylinder, and a pressure applying member having a second bone engaging surface coupled to the pistons opposite the first bone engaging surface.

22. The method of claim 21, wherein said hydraulically distracting further comprises:
   extending the at least one extendable member by delivery of hydraulic fluid thereto under sufficient pressure to reposition at least one said vertebral body by extension of said at least one extendable member.

23. The method of claim 22, wherein said rigidly fixing comprises:
   delivering a hydraulic fluid comprising a curable polymer; and
   allowing the curable polymer to cure within the extendable member.

24. The method of claim 2, wherein said inserting comprises engaging an insertion handle with said implant and positioning the implant between the two vertebral bodies by manipulating the insertion handle.

25. The method of claim 24, wherein the hydraulic fluid is delivered through said insertion handle.

* * * * *